US009223936B2

(12) United States Patent
Aragones et al.

(10) Patent No.: US 9,223,936 B2
(45) Date of Patent: Dec. 29, 2015

(54) FATIGUE INDICES AND USES THEREOF

(75) Inventors: Tesa Aragones, Portland, OR (US); Annie Chen, Portland, OR (US); Adriana Guerrero, Beaverton, OR (US); Christina S. Self, Portland, OR (US); Jay C. Blahnik, Laguna Beach, CA (US); Paul T. Winsper, Beaverton, OR (US)

(73) Assignee: NIKE, Inc., Beaverton, OR (US)

( * ) Notice: Subject to any disclaimer, the term of this patent is extended or adjusted under 35 U.S.C. 154(b) by 0 days.

(21) Appl. No.: 13/304,056

(22) Filed: Nov. 23, 2011

(65) Prior Publication Data

US 2012/0271143 A1    Oct. 25, 2012

Related U.S. Application Data

(63) Continuation-in-part of application No. 13/290,359, filed on Nov. 7, 2011, and a continuation-in-part of application No. 13/290,478, filed on Nov. 7, 2011.

(60) Provisional application No. 61/417,102, filed on Nov. 24, 2010, provisional application No. 61/422,511, (Continued)

(51) Int. Cl.
    G09B 19/00    (2006.01)
    A63B 5/16    (2006.01)
    G06F 19/00    (2011.01)

(52) U.S. Cl.
    CPC ........ *G06F 19/3481* (2013.01); *G09B 19/0038* (2013.01)

(58) Field of Classification Search
    CPC .... G09B 19/00; G09B 19/38; G09B 19/0076; A63B 5/16; A63B 5/18; A63B 21/0053; A63B 21/0058; A63B 21/153; A63B 22/02; A63B 22/08; A63B 22/0023; A63B 24/00; A63B 24/0003; A63B 24/0006; A63B 24/0062; A63B 69/00; A63B 69/36; A63B 71/0622; A63B 2208/12; A63B 2220/16; A63B 2220/51; A63B 2220/80; A63B 2220/806; A63B 2021/0026; A63B 2024/0012
    USPC ........... 434/247, 257, 258; 482/4–8, 901, 902
    See application file for complete search history.

(56) References Cited

U.S. PATENT DOCUMENTS 5,277,197 A    1/1994    Church et al.
5,288,078 A    2/1994    Capper et al.
(Continued)

FOREIGN PATENT DOCUMENTS

DE    29720110 U1    1/1998
GB    2415788    1/2006
(Continued)

OTHER PUBLICATIONS

International Searching Authority, "International Search Report and Written Opinion," issued in connection with international application serial No. PCT/US2012/066070, mailed May 31, 2013, 9 pages.

(Continued)

*Primary Examiner* — Nikolai A Gishnock
(74) *Attorney, Agent, or Firm* — Banner & Witcoff, Ltd.

(57) ABSTRACT

Example embodiments may relate to a system, method, apparatus, and computer readable media configured for monitoring a user performing an athletic movement and/or exercise and generating a fatigue value. Fatigue values may be determined for different groups. In one embodiment, a first value is determined for a muscle fatigue value and a second value is determined for a respiratory value. In another embodiment, a first value may pertain to a first muscle group and a second value may pertain to a second muscle group. A fatigue index may be created from values obtained during an athletic movement and/or a workout session. In further embodiments, a cumulative fatigue index may be determined. A cumulative fatigue index may consider values obtained during several workout sessions. Further, data obtained outside of workout sessions may be considered in determinations relating to fatigue values and/or indices.

20 Claims, 15 Drawing Sheets

Related U.S. Application Data filed on Dec. 13, 2010, provisional application No. 61/432,472, filed on Jan. 13, 2011, provisional application No. 61/433,792, filed on Jan. 18, 2011.

(56) References Cited

U.S. PATENT DOCUMENTS

| | | |
|---|---|---|
| 5,335,188 A | 8/1994 | Brisson |
| 5,524,637 A | 6/1996 | Erickson |
| 5,527,239 A | 6/1996 | Abbondanza |
| 5,598,849 A | 2/1997 | Browne |
| 5,655,316 A | 8/1997 | Huang |
| 5,667,459 A * | 9/1997 | Su ................................... 482/4 |
| 5,688,137 A | 11/1997 | Bustance |
| 5,791,351 A | 8/1998 | Curchod |
| 5,836,770 A | 11/1998 | Powers |
| 5,846,086 A * | 12/1998 | Bizzi et al. .................... 434/247 |
| 5,904,484 A | 5/1999 | Burns |
| 5,913,727 A | 6/1999 | Ahdoot |
| 5,955,957 A | 9/1999 | Calabrese et al. |
| 6,126,449 A | 10/2000 | Burns |
| 6,308,565 B1 | 10/2001 | French et al. |
| 6,316,934 B1 | 11/2001 | Amorai-Moriya et al. |
| 6,428,449 B1 | 8/2002 | Apseloff |
| 6,516,222 B2 | 2/2003 | Fukuda |
| 6,743,167 B2 | 6/2004 | Balkin et al. |
| 6,765,726 B2 | 7/2004 | French et al. |
| 6,788,200 B1 | 9/2004 | Jamel et al. |
| 6,836,744 B1 | 12/2004 | Asphahani et al. |
| 6,876,496 B2 | 4/2005 | French et al. |
| 7,018,211 B1 | 3/2006 | Birkholzer et al. |
| 7,079,889 B2 | 7/2006 | Nakada |
| 7,163,490 B2 | 1/2007 | Chen |
| 7,192,401 B2 | 3/2007 | Saalasti et al. |
| 7,254,516 B2 | 8/2007 | Case, Jr. et al. |
| 7,265,666 B2 | 9/2007 | Daniel |
| 7,359,121 B2 | 4/2008 | French et al. |
| 7,493,232 B1 | 2/2009 | Surina |
| 7,497,807 B2 | 3/2009 | Neff et al. |
| 7,497,812 B2 | 3/2009 | Neff et al. |
| 7,556,590 B2 | 7/2009 | Watterson et al. |
| 7,628,730 B1 | 12/2009 | Watterson et al. |
| 7,736,272 B2 | 6/2010 | Martens |
| 7,783,347 B2 | 8/2010 | Abourizk et al. |
| 7,789,800 B1 | 9/2010 | Watterson et al. |
| 7,846,067 B2 | 12/2010 | Hanoun et al. |
| 7,846,069 B2 | 12/2010 | Martens |
| 7,927,253 B2 | 4/2011 | Vincent et al. |
| 7,967,728 B2 | 6/2011 | Zavadsky et al. |
| 7,985,164 B2 | 7/2011 | Ashby |
| 8,012,064 B2 | 9/2011 | Martens |
| 8,029,411 B2 | 10/2011 | Johnson |
| 8,038,578 B2 | 10/2011 | Olrik et al. |
| 8,118,710 B2 | 2/2012 | Weinman et al. |
| 8,230,367 B2 | 7/2012 | Bell et al. |
| 8,235,870 B2 | 8/2012 | Hamilton |
| 8,284,157 B2 | 10/2012 | Markovic et al. |
| 8,284,847 B2 | 10/2012 | Adermann |
| 8,409,057 B2 | 4/2013 | Martens |
| 8,460,199 B2 | 6/2013 | Rulkov et al. |
| 8,503,086 B2 | 8/2013 | French et al. |
| 8,568,277 B2 | 10/2013 | Johnson |
| 8,568,330 B2 | 10/2013 | Mollicone et al. |
| 8,758,201 B2 | 6/2014 | Ashby et al. |
| 8,784,270 B2 | 7/2014 | Ashby et al. |
| 8,812,428 B2 | 8/2014 | Mollicone et al. |
| 8,858,400 B2 | 10/2014 | Johnson |
| 8,861,091 B2 | 10/2014 | French et al. |
| 9,008,973 B2 | 4/2015 | French |
| 2002/0019258 A1 | 2/2002 | Kim et al. |
| 2003/0040348 A1 | 2/2003 | Martens |
| 2003/0054327 A1 | 3/2003 | Evensen |
| 2004/0087366 A1 | 5/2004 | Shum et al. |
| 2004/0102931 A1 | 5/2004 | Ellis et al. |
| 2004/0162194 A1 | 8/2004 | Habing |
| 2005/0079905 A1 | 4/2005 | Martens |
| 2005/0085348 A1 | 4/2005 | Kiefer et al. |
| 2005/0113650 A1 | 5/2005 | Pacione et al. |
| 2005/0272517 A1 | 12/2005 | Funk et al. |
| 2006/0040793 A1 | 2/2006 | Martens |
| 2006/0079800 A1 | 4/2006 | Martikka et al. |
| 2006/0205569 A1 | 9/2006 | Watterson et al. |
| 2006/0229170 A1 | 10/2006 | Ozawa et al. |
| 2006/0247070 A1 | 11/2006 | Funk et al. |
| 2007/0050715 A1 | 3/2007 | Behar |
| 2007/0232453 A1 | 10/2007 | Hanoun |
| 2007/0232455 A1 | 10/2007 | Hanoun |
| 2007/0272011 A1 | 11/2007 | Chapa et al. |
| 2008/0189291 A1 | 8/2008 | Hsu |
| 2008/0200312 A1 | 8/2008 | Tagliabue |
| 2009/0044429 A1 | 2/2009 | Cook et al. |
| 2009/0149299 A1 | 6/2009 | Tchao et al. |
| 2009/0171614 A1 | 7/2009 | Damen |
| 2009/0269728 A1 | 10/2009 | Verstegen et al. |
| 2009/0298650 A1 | 12/2009 | Kutliroff |
| 2009/0299232 A1 | 12/2009 | Lanfermann et al. |
| 2010/0063778 A1 | 3/2010 | Schrock et al. |
| 2010/0125026 A1 | 5/2010 | Zavadsky et al. |
| 2010/0125028 A1 | 5/2010 | Heppert |
| 2010/0137748 A1 | 6/2010 | Sone et al. |
| 2010/0144414 A1 | 6/2010 | Edis et al. |
| 2010/0197462 A1 | 8/2010 | Piane, Jr. |
| 2010/0210359 A1 | 8/2010 | Krzeslo et al. |
| 2010/0227302 A1 | 9/2010 | McGilvery et al. |
| 2010/0234184 A1 | 9/2010 | Le Page et al. |
| 2010/0248901 A1 | 9/2010 | Martens |
| 2010/0302142 A1 | 12/2010 | French et al. |
| 2010/0316983 A1 | 12/2010 | Johns, Jr. |
| 2010/0332243 A1 | 12/2010 | Weigman et al. |
| 2011/0077129 A1 | 3/2011 | Martens et al. |
| 2011/0111922 A1 | 5/2011 | Weinman et al. |
| 2011/0111924 A1 * | 5/2011 | Jones et al. ....................... 482/8 |
| 2011/0112771 A1 | 5/2011 | French |
| 2011/0136627 A1 | 6/2011 | Williams |
| 2011/0212791 A1 | 9/2011 | Ueda et al. |
| 2011/0229864 A1 | 9/2011 | Short et al. |
| 2011/0251021 A1 | 10/2011 | Zavadsky et al. |
| 2011/0270135 A1 | 11/2011 | Dooley et al. |
| 2011/0306491 A1 | 12/2011 | Belisle |
| 2011/0307821 A1 | 12/2011 | Martens |
| 2012/0034971 A1 | 2/2012 | Harp et al. |
| 2012/0038627 A1 | 2/2012 | Sung et al. |
| 2012/0130886 A1 | 5/2012 | Shergill et al. |
| 2012/0234111 A1 | 9/2012 | Molyneux et al. |
| 2012/0315986 A1 | 12/2012 | Walling |
| 2012/0315987 A1 | 12/2012 | Walling |
| 2013/0019694 A1 | 1/2013 | Molyneux et al. |
| 2013/0022947 A1 | 1/2013 | Muniz Simas et al. |
| 2013/0022950 A1 | 1/2013 | Muniz Simas et al. |
| 2013/0108993 A1 | 5/2013 | Katz |
| 2013/0281796 A1 | 10/2013 | Pan |
| 2013/0295539 A1 | 11/2013 | Wilson et al. |
| 2013/0338802 A1 | 12/2013 | Winsper et al. |
| 2014/0073486 A1 | 3/2014 | Ahmed et al. |

FOREIGN PATENT DOCUMENTS

| | | |
|---|---|---|
| JP | 2000504854 A | 4/2000 |
| JP | 2001231904 A | 8/2001 |
| JP | 2001299975 A | 10/2001 |
| JP | 2002112984 A | 4/2002 |
| JP | 2002291952 A | 10/2002 |
| JP | 2003290406 A | 10/2003 |
| JP | 2004089727 A | 3/2004 |
| JP | 3656853 B2 | 6/2005 |
| JP | 2005198818 A | 7/2005 |
| JP | 2006263002 A | 10/2006 |
| JP | 2006320424 A | 11/2006 |
| JP | 2008295746 A | 12/2008 |
| JP | 2009048757 A | 3/2009 |
| JP | 2009213782 A | 9/2009 |
| JP | 2009219828 A | 10/2009 |
| KR | 20030041034 A | 5/2003 |

(56) References Cited

FOREIGN PATENT DOCUMENTS

| KR | 20090084035 A | 8/2009 |
|---|---|---|
| WO | 9729814 A1 | 8/1997 |
| WO | 2004073494 A2 | 9/2004 |
| WO | 2009043024 A1 | 4/2009 |
| WO | 2009/073607 A2 | 6/2009 |
| WO | 2012/071548 A1 | 5/2012 |
| WO | 2012/071551 A1 | 5/2012 |
| WO | 2012061804 A1 | 5/2012 |

OTHER PUBLICATIONS

United States Patent and Trademark Office, "Non-Final Office Action," issued in connection with U.S. Appl. No. 13/290,359, mailed Jun. 20, 2013, 11 pages.

United States Patent and Trademark Office, "Non-Final Office Action," issued in connection with U.S. Appl. No. 13/290,478, mailed Jun. 20, 2013, 8 pages.

United States Patent and Trademark Office, "Non-Final Office Action," issued in connection with U.S. Appl. No. 13/304,064, mailed Jun. 20, 2013, 10 pages.

International Bureau, "International Preliminary Report on Patentability," issued in connection with international application serial No. PCT/US2011/064711, mailed Jun. 27, 2013, 6 pages.

United States Patent and Trademark Office, "Final Office Action," issued in connection with U.S. Appl. No. 13/304,064, mailed Oct. 24, 2013, 13 pages.

May 29, 2013 (WO)—International Search Report and Written Opinion—App. No. PCT/US2012/066065.

Jun. 6, 2013 (WO)—International Preliminary Report on Patentability—App. No. PCT/US20111062117.

May 16, 2013 (WO)—International Preliminary Report on Patentability—App. No. PCT/US20111059559.

Apr. 3, 2012 (WO)—International Search Report and Written Opinion—Application No. PCT/US20111064711.

Feb. 23, 2012 W(O)—International Search Report and Written Opinion—App. No. PCT/US2011/062117.

Feb. 20, 2014 (WO)—International Search Report and Written Opinion—App. No. PCT/US2013/067512.

Sep. 12, 2013(WO)—ISR and WO—App. No. PCT/US2013/044109.

United States Patent and Trademark Office, "Non-Final Office Action," issued in connection with U.S. Appl. No. 13/894,088, mailed Aug. 6, 2013, 5 pages.

\* cited by examiner

FATIGUE INDICES AND USES THEREOF

CROSS REFERENCE TO RELATED APPLICATIONS

This application claims the benefit of, and priority to, U.S. Provisional Patent Application Nos. 61/417,102 filed Nov. 24, 2010, 61/422,511 filed Dec. 13, 2010, 61/432,472 filed Jan. 13, 2011, and 61/433,792 filed Jan. 18, 2011, each of which is entitled "Method and System for Automated Personal Training" The content of each of the provisional applications is expressly incorporated herein by reference in its entirety for any and all non-limiting purposes. This application is a continuation-in-part of, and claims the benefit of, and priority to, U.S. Non-Provisional patent application Ser. Nos. 13/290,359 and 13/290,478, each entitled "Method and System for Automated Personal Training" and filed Nov. 7, 2011. The content of each of the non-provisional applications is expressly incorporated herein by reference in its entirety for any and all non-limiting purposes.

BACKGROUND

While most people appreciate the importance of physical fitness, many have difficulty finding the motivation required to maintain a regular exercise program. Some people find it particularly difficult to maintain an exercise regimen that involves continuously repetitive motions, such as running, walking and bicycling.

Additionally, individuals may view exercise as work or a chore and thus, separate it from enjoyable aspects of their daily lives. Often, this separation between athletic activity and other activities reduces the amount of motivation that an individual might have toward exercising. Further, athletic activity services and systems directed toward encouraging individuals to engage in athletic activities might also be too focused on one or more particular activities while an individual's interests are ignored. This may further decrease a user's interest in participating in athletic activities or using the athletic activity services and systems.

Therefore, improved systems and methods to address these and other shortcomings in the art are desired.

BRIEF SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

Aspects of this disclosure relate to motivating individuals to obtain or maintain a threshold level of physical activity. Certain implementations may motivate individuals to participate in a regular exercise program. In one embodiment, feedback may facilitate individuals observing one or more benefits associated with physical activity. By realizing benefits associated with their activities, users may be encouraged to continue exercising, such as through participation in one or more regular activities.

One or more fatigue values may be calculated during an athletic movement. In further embodiments, a plurality of fatigue values may be determined for an exercise routine comprising a plurality of athletic movements. Fatigue values may be determined for different groups. In one embodiment, a first value is determined for a muscle fatigue value and a second value is determined for a respiratory value. In another embodiment, a first value may pertain to a first muscle group and a second value may pertain to a second muscle group. A fatigue index may be created from values obtained during an athletic movement and/or a workout session. In further embodiments, a cumulative fatigue index may be determined. A cumulative fatigue index may consider values obtained during several workout sessions. Further, data obtained outside of workout sessions may be considered in determinations relating to fatigue values and/or indices.

Example embodiments may relate to a system, method, apparatus, and computer readable media configured for monitoring a user performing an exercise and generating a representation of a user and a virtual shadow. According to one implementation, the virtual shadow may illustrate a proper form (or any specific form) of the exercise. Further aspects relate to estimating a fatigue value. Fatigue values may be determined by comparing a user's form to the proper form.

These and other aspects of the embodiments are discussed in greater detail throughout this disclosure, including the accompanying drawings.

BRIEF DESCRIPTION OF THE DRAWINGS

The present disclosure is illustrated by way of example and not limited in the accompanying figures in which like reference numerals indicate similar elements and in which:

FIGS. 1A-B illustrate an example of a system for providing personal training in accordance with example embodiments, wherein FIG. 1A illustrates an example network configured to monitor athletic activity, and FIG. 1B illustrates an example computing device in accordance with example embodiments.

DETAILED DESCRIPTION

In the following description of the various embodiments, reference is made to the accompanying drawings, which form a part hereof, and in which is shown by way of illustration various embodiments in which the disclosure may be practiced. It is to be understood that other embodiments may be utilized and structural and functional modifications may be made without departing from the scope and spirit of the present disclosure. Further, headings within this disclosure should not be considered as limiting aspects of the disclosure. Those skilled in the art with the benefit of this disclosure will appreciate that the example embodiments are not limited to the example headings.

I. Example Personal Training System

A. Illustrative Computing Devices

Figure 1A:
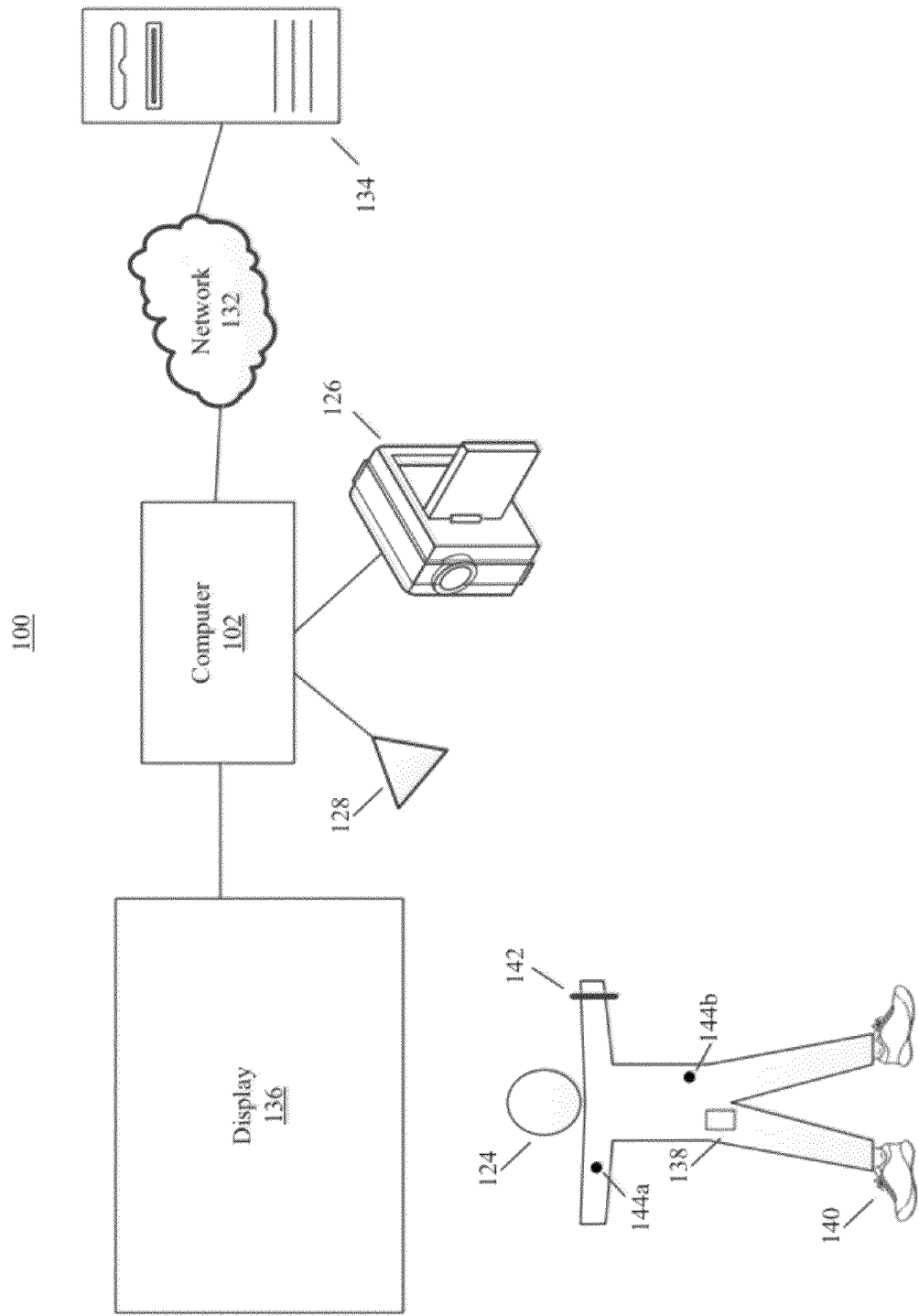

FIG. 1A illustrates an example of a personal training system 100 in accordance with example embodiments. Example system 100 may include one or more electronic devices, such as computer 102. Computer 102 may comprise a mobile terminal, such as a telephone, music player, tablet, netbook or any portable device. In other embodiments, computer 102 may comprise a set-top box (STB), desktop computer, digital video recorder(s) (DVR), computer server(s), and/or any other desired computing device. In certain configurations, computer 102 may comprise a gaming console, such as for example, a Microsoft® XBOX, Sony® PlayStation, and/or a Nintendo® Wii gaming consoles. Those skilled in the art will appreciate that these are merely example consoles for descriptive purposes and this disclosure is not limited to any console or device.

Figure 1B:
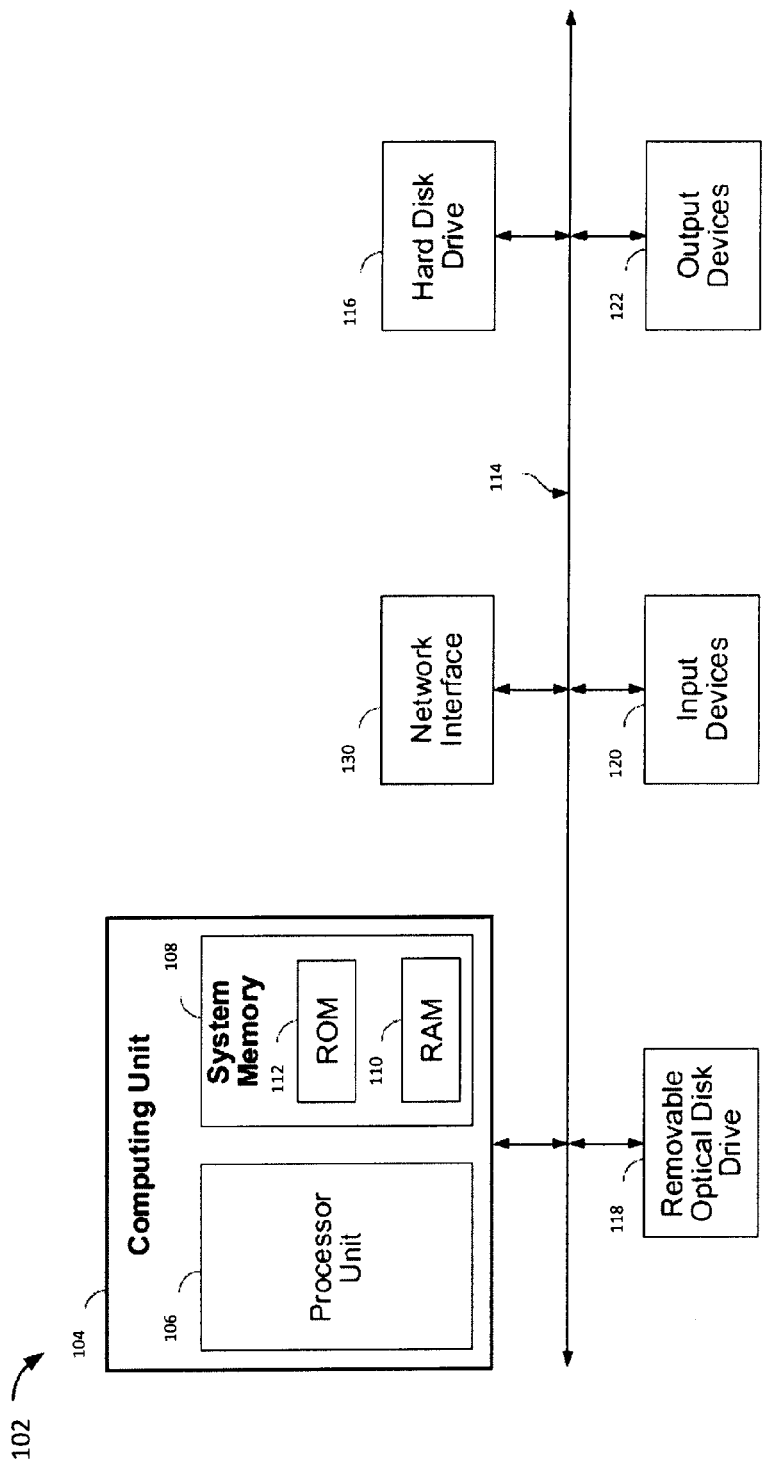

Turning briefly to FIG. 1B, computer 102 may include computing unit 104, which may comprise at least one processing unit 106. Processing unit 106 may be any type of processing device for executing software instructions, such as for example, a microprocessor device. Computer 102 may include a variety of non-transitory computer readable media, such as memory 108. Memory 108 may include, but is not limited to, random access memory (RAM) such as RAM 110, and/or read only memory (ROM), such as ROM 112. Memory 108 may include any of: electronically erasable programmable read only memory (EEPROM), flash memory or other memory technology, CD-ROM, digital versatile disks (DVD) or other optical disk storage, magnetic storage devices, or any other medium that can be used to store the desired information and that can be accessed by computer 102.

The processing unit 106 and the system memory 108 may be connected, either directly or indirectly, through a bus 114 or alternate communication structure to one or more peripheral devices. For example, the processing unit 106 or the system memory 108 may be directly or indirectly connected to additional memory storage, such as a hard disk drive 116, a removable magnetic disk drive, an optical disk drive 118, and a flash memory card, as well as to input devices 120, and output devices 122. The processing unit 106 and the system memory 108 also may be directly or indirectly connected to one or more input devices 120 and one or more output devices 122. The output devices 122 may include, for example, a monitor display, television, printer, stereo, or speakers. The input devices 120 may include, for example, a keyboard, touch screen, a remote control pad, a pointing device (such as a mouse, touchpad, stylus, trackball, or joystick), a scanner, a camera or a microphone. In this regard, input devices 120 may comprise one or more sensors configured to sense, detect, and/or measure athletic movement from a user, such as user 124, shown in FIG. 1A. As used herein, an "athletic movement" includes movements relating to fitness, exercise, flexibility, including movements that may be part of one or more single and multiple participant athletic competitions, exercise routines, and/or combinations thereof.

Looking again to FIG. 1A, image-capturing device 126 and/or sensor 128 may be utilized in detecting and/or measuring athletic movements of user 124. In one embodiment, data obtained image-capturing device 126 or sensor 128 may directly detect athletic movements, such that the data obtained from image-capturing device 126 or sensor 128 is directly correlated to a motion parameter. For example, and with reference to FIG. 4, image data from image-capturing device 126 may detect that the distance between sensor locations 402g and 402i has decreased and therefore, image-capturing device 126 alone may be configured to detect that user's 124 right arm has moved. Yet, in other embodiments, data from image-capturing device 126 and/or sensor 128 may be utilized in combination, either with each other or with other sensors to detect and/or measure movements. Thus, certain measurements may be determined from combining data obtained from two or more devices. Image-capturing device 126 and/or sensor 128 may include or be operatively connected to one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Example uses of illustrative sensors 126, 128 are provided below in Section I.C, entitled "Illustrative Sensors." Computer 102 may also use touch screens or image capturing device to determine where a user is pointing to make selections from a graphical user interface. One or more embodiments may utilize one or more wired and/or wireless technologies, alone or in combination, wherein examples of wireless technologies include Bluetooth® technologies, Bluetooth® low energy technologies, and/or ANT technologies.

B. Illustrative Network

Still further, computer 102, computing unit 104, and/or any other electronic devices may be directly or indirectly connected to one or more network interfaces, such as example interface 130 (shown in FIG. 1B) for communicating with a network, such as network 132. In the example of FIG. 1B, network interface 130, may comprise a network adapter or network interface card (NIC) configured to translate data and control signals from the computing unit 104 into network messages according to one or more communication protocols, such as the Transmission Control Protocol (TCP), the Internet Protocol (IP), and the User Datagram Protocol (UDP). These protocols are well known in the art, and thus will not be discussed here in more detail. An interface 130 may employ any suitable connection agent for connecting to a network, including, for example, a wireless transceiver, a power line adapter, a modem, or an Ethernet connection. Network 132, however, may be any one or more information distribution network(s), of any type(s) or topography(s), alone or in combination(s), such as internet(s), intranet(s), cloud(s), LAN(s). Network 132 may be any one or more of cable, fiber, satellite, telephone, cellular, wireless, etc. Networks are well known in the art, and thus will not be discussed here in more detail. Network 132 may be variously configured such as having one or more wired or wireless communication channels to connect one or more locations (e.g., schools, businesses, homes, consumer dwellings, network resources, etc.), to one or more remote servers 134, or to other computers, such as similar or identical to computer 102. Indeed, system 100 may include more than one instance of each component (e.g., more than one computer 102, more than one display 136, etc.). In this regard, although display 136 is presented in FIG. 1A as a screen, in further embodiments, one or more display devices (such as display 136) may be incorporated into eyewear. The display devices incorporated into eyewear may provide feedback to users, such as through one or processes discussed herein. Eyewear incorporating one or more display devices may provide for a portable display system.

Regardless of whether computer 102 or other electronic device within network 132 is portable or at a fixed location, it should be appreciated that, in addition to the input, output and storage peripheral devices specifically listed above, the computing device may be connected, such as either directly, or through network 132 to a variety of other peripheral devices, including some that may perform input, output and storage functions, or some combination thereof. In certain embodiments, a single device may integrate one or more components shown in FIG. 1A. For example, a single device may include computer 102, image-capturing device 126, sensor 128, display 136 and/or additional components. In one embodiment, sensor device 138 may comprise a mobile terminal having a display 136, image-capturing device 126, and one or more sensors 128. Yet, in another embodiment, image-capturing device 126, and/or sensor 128 may be peripherals configured to be operatively connected to a media device, including for example, a gaming or media system. Thus, it goes from the foregoing that this disclosure is not limited to stationary systems and methods. Rather, certain embodiments may be carried out by a user 124 in almost any location.

C. Illustrative Sensors

Computer 102 and/or other devices may comprise one or more sensors 126, 128 configured to detect and/or monitor at least one fitness parameter of a user 124. Sensors 126 and/or 128, may include but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. Network 132 and/or computer 102 may be in communication with one or more electronic devices of system 100, including for example, display 136, an image capturing device 126 (e.g., one or more video cameras), and sensor 128, which may be an infrared (IR) device. In one embodiment sensor 128 may comprise an IR transceiver. For example, sensors 126, and/or 128 may transmit waveforms into the environment, including towards the direction of user 124 and receive a "reflection" or otherwise detect alterations of those released waveforms. In yet another embodiment, image-capturing device 126 and/or sensor 128 may be configured to transmit and/or receive other wireless signals, such as radar, sonar, and/or audible information. Those skilled in the art will readily appreciate that signals corresponding to a multitude of different data spectrums may be utilized in accordance with various embodiments. In this regard, sensors 126 and/or 128 may detect waveforms emitted from external sources (e.g., not system 100). For example, sensors 126 and/or 128 may detect heat being emitted from user 124 and/or the surrounding environment. Thus, image-capturing device 126 and/or sensor 128 may comprise one or more thermal imaging devices. In one embodiment, image-capturing device 126 and/or sensor 128 may comprise an IR device configured to perform range phenomenology. As a non-limited example, image-capturing devices configured to perform range phenomenology are commercially available from Flir Systems, Inc. of Portland, Oreg. Although image capturing device 126 and sensor 128 and display 136 are shown in direct (wirelessly or wired) communication with computer 102, those skilled in the art will appreciate that any may directly communicate (wirelessly or wired) with network 132.

1. Multi-Purpose Electronic Devices

User 124 may possess, carry, and/or wear any number of electronic devices, including sensory devices 138, 140, 142, and/or 144. In certain embodiments, one or more devices 138, 140, 142, 144 may not be specially manufactured for fitness or athletic purposes. Indeed, aspects of this disclosure relate to utilizing data from a plurality of devices, some of which are not fitness devices, to collect, detect, and/or measure athletic data. In one embodiment, device 138 may comprise a portable electronic device, such as a telephone or digital music player, including an IPOD®, IPAD®, or iPhone®, brand devices available from Apple, Inc. of Cupertino, Calif. or Zune® or Microsoft® Windows devices available from Microsoft of Redmond, Wash. As known in the art, digital media players can serve as both an output device for a computer (e.g., outputting music from a sound file or pictures from an image file) and a storage device. In one embodiment, device 138 may be computer 102, yet in other embodiments, computer 102 may be entirely distinct from device 138. Regardless of whether device 138 is configured to provide certain output, it may serve as an input device for receiving sensory information. Devices 138, 140, 142, and/or 144 may include one or more sensors, including but not limited to: an accelerometer, a gyroscope, a location-determining device (e.g., GPS), light sensor, temperature sensor (including ambient temperature and/or body temperature), heart rate monitor, image-capturing sensor, moisture sensor and/or combinations thereof. In certain embodiments, sensors may be passive, such as reflective materials that may be detected by image-capturing device 126 and/or sensor 128 (among others). In certain embodiments, sensors 144 may be integrated into apparel, such as athletic clothing. For instance, the user 124 may wear one or more on-body sensors 144*a-b*. Sensors 144 may be incorporated into the clothing of user 124 and/or placed at any desired location of the body of user 124. Sensors 144 may communicate (e.g., wirelessly) with computer 102, sensors 128, 138, 140, and 142, and/or camera 126. Examples of interactive gaming apparel are described in U.S. patent application Ser. No. 10/286,396, filed Oct. 30, 2002, and published as U.S. Pat. Pub, No. 2004/0087366, the contents of which are incorporated herein by reference in its entirety for any and all non-limiting purposes. In certain embodiments, passive sensing surfaces may reflect waveforms, such as infrared light, emitted by image-capturing device 126 and/or sensor 128. In one embodiment, passive sensors located on user's 124 apparel may comprise generally spherical structures made of glass or other transparent or translucent surfaces which may reflect waveforms. Different classes of apparel may be utilized in which a given class of apparel has specific sensors configured to be located proximate to a specific portion of the user's 124 body when properly worn. For example, golf apparel may include one or more sensors positioned on the apparel in a first configuration and yet soccer apparel may include one or more sensors positioned on apparel in a second configuration. For example, looking briefly to FIG. 14, golf apparel may have more sensors positioned about regions 1402A and 1402D than apparel for soccer, which may have more sensors (and/or different types of sensors) positioned about regions 1402C and 1402F). Devices 138-144 may communicate with each other, either directly or through a network, such as network 132. Communication between one or more of devices 138-144 may communicate through computer 102. For example, two or more of devices 138-144 may be peripherals operatively connected to bus 114 of computer 102. In yet another embodiment, a first device, such as device 138 may communicate with a first computer, such as computer 102 as well as another device, such as device 142, however, device 142 may not be configured to connect to computer 102 but may communicate with device 138. Those skilled in the art will appreciate that other configurations are possible.

Some implementations of the example embodiments may alternately or additionally employ computing devices that are intended to be capable of a wide variety of functions, such as a desktop or laptop personal computer. These computing devices may have any combination of peripheral devices or additional components as desired. Also, the components shown in FIG. 1B may be included in the server 134, other computers, apparatuses, etc.

2. Illustrative Apparel/Accessory Sensors

In certain embodiments, sensory devices 138, 140, 142 and/or 144 may be formed within or otherwise associated with user's 124 clothing or accessories, including a watch, armband, wristband, necklace, shirt, shoe, or the like. Examples of shoe-mounted and wrist-worn devices (devices 140 and 142, respectively) are described immediately below, however, these are merely example embodiments and this disclosure should not be limited to such.

i. Shoe-Mounted Device

In certain embodiments, sensory device 140 may comprise footwear which may include one or more sensors, including but not limited to: an accelerometer, location-sensing components, such as GPS, and/or a force sensor system. FIG. 2A illustrates one exemplary embodiment of an example sensor system 202. In certain embodiments, system 202 may include a sensor assembly 204. Assembly 204 may comprise one or more sensors, such as for example, an accelerometer, location-determining components, and/or force sensors. In the illustrated embodiment, assembly 204 incorporates a plurality of sensors, which may include force-sensitive resistor (FSR) sensors 206. In yet other embodiments, other sensor(s) may be utilized. Port 208 may be positioned within a sole structure 209 of a shoe. Port 208 may optionally be provided to be in communication with an electronic module 210 (which maybe in a housing 211) and a plurality of leads 212 connecting the FSR sensors 206 to the port 208. Module 210 may be contained within a well or cavity in a sole structure of a shoe. The port 208 and the module 210 include complementary interfaces 214, 216 for connection and communication.

In certain embodiments, at least one force-sensitive resistor 206 shown in FIG. 2A may contain first and second electrodes or electrical contacts 218, 220 and a force-sensitive resistive material 222 and/or 224 disposed between the electrodes 218, 220 to electrically connect the electrodes 218, 220 together. When pressure is applied to the force-sensitive material 222/224, the resistivity and/or conductivity of the force-sensitive material 222/224 changes, which changes the electrical potential between the electrodes 218, 220. The change in resistance can be detected by the sensor system 202 to detect the force applied on the sensor 216. The force-sensitive resistive material 222/224 may change its resistance under pressure in a variety of ways. For example, the force-sensitive material 222/224 may have an internal resistance that decreases when the material is compressed, similar to the quantum tunneling composites described in greater detail below. Further compression of this material may further decrease the resistance, allowing quantitative measurements, as well as binary (on/off) measurements. In some circumstances, this type of force-sensitive resistive behavior may be described as "volume-based resistance," and materials exhibiting this behavior may be referred to as "smart materials." As another example, the material 222/224 may change the resistance by changing the degree of surface-to-surface contact. This can be achieved in several ways, such as by using micro projections on the surface that raise the surface resistance in an uncompressed condition, where the surface resistance decreases when the micro projections are compressed, or by using a flexible electrode that can be deformed to create increased surface-to-surface contact with another electrode. This surface resistance may be the resistance between the material 222 and the electrode 218, 220 and/or the surface resistance between a conducting layer (e.g. carbon/graphite) and a force-sensitive layer (e.g. a semiconductor) of a multi-layer material 222/224. The greater the compression, the greater the surface-to-surface contact, resulting in lower resistance and enabling quantitative measurement. In some circumstances, this type of force-sensitive resistive behavior may be described as "contact-based resistance." It is understood that the force-sensitive resistive material 222/224, as defined herein, may be or include a doped or non-doped semiconducting material.

The electrodes 218, 220 of the FSR sensor 206 can be formed of any conductive material, including metals, carbon/graphite fibers or composites, other conductive composites, conductive polymers or polymers containing a conductive material, conductive ceramics, doped semiconductors, or any other conductive material. The leads 212 can be connected to the electrodes 218, 220 by any suitable method, including welding, soldering, brazing, adhesively joining, fasteners, or any other integral or non-integral joining method. Alternately, the electrode 218, 220 and associated lead(s) 212 may be formed of a single piece of the same material 222/224. In further embodiments, material 222 is configured to have at least one electric property (e.g., conductivity, resistance, etc.) than material 224. Examples of exemplary sensors are disclosed in U.S. patent application Ser. No. 12/483,824, filed on Jun. 12, 2009, the contents of which are incorporated herein in their entirety for any and all non-limiting purposes.

ii. Wrist-Worn Device

Figure 2B:
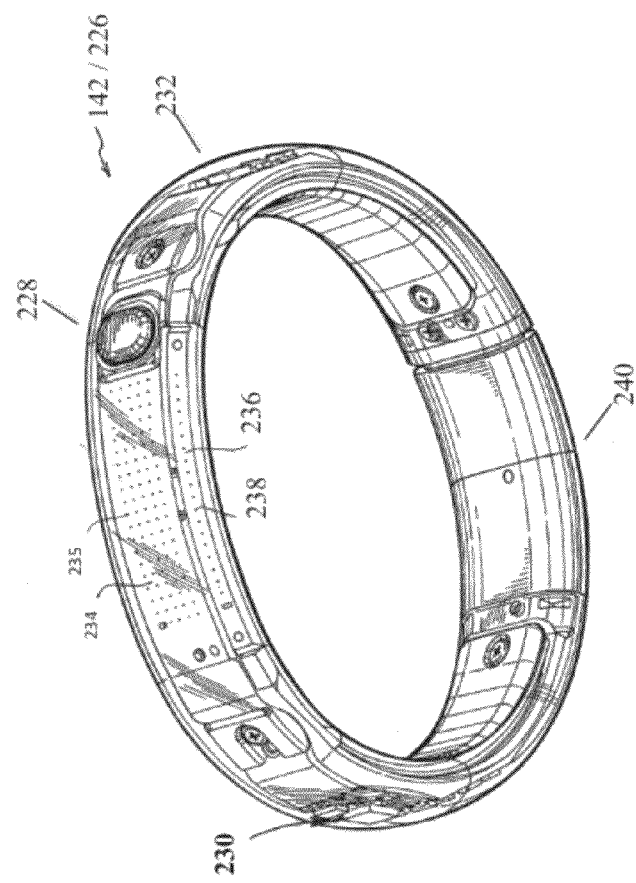
FIGS. 2A-B illustrate example sensor assemblies that may be worn by a user in accordance with example embodiments.
Figure 2A:
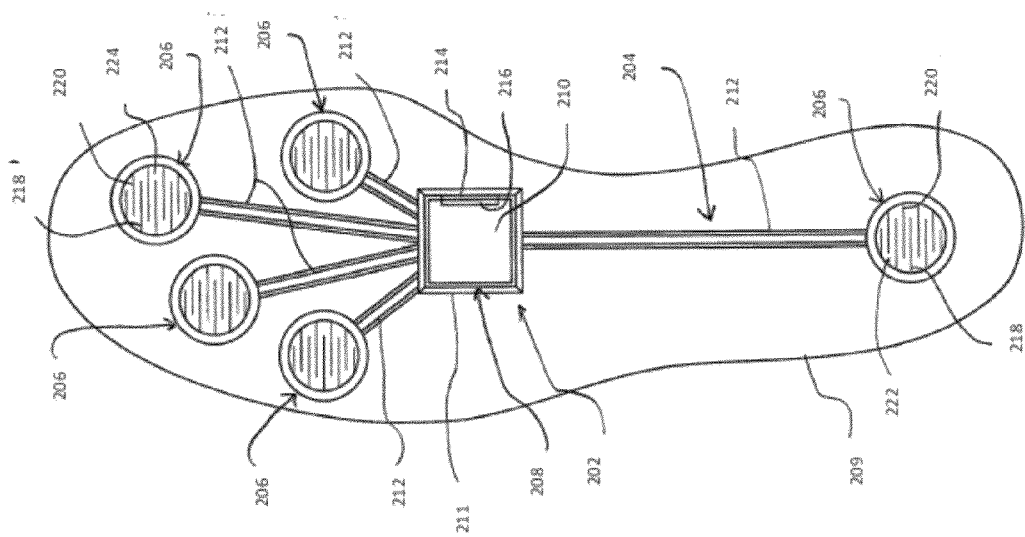

As shown in FIG. 2B, device 226 (which may be, or be a duplicative of or resemble sensory device 142 shown in FIG. 1A) may be configured to be worn by user 124, such as around a wrist, arm, ankle or the like. Device 226 may monitor movements of a user, including, e.g., athletic movements or other activity of user 124. For example, in one embodiment, device 226 may be activity monitor that measures, monitors, tracks or otherwise senses the user's activity (or inactivity) regardless of the user's proximity or interactions with computer 102. Device 226 may detect athletic movement or other activity (or inactivity) during user's 124 interactions with computer 102 and/or operate independently of computer 102. Device 226 may communicate directly or indirectly, wired or wirelessly, with network 132 and/or other devices, such as devices 138 and/or 140. Athletic data obtained from device 226 may be utilized in determinations conducted by computer 102, such as determinations relating to which exercise programs are presented to user 124. As used herein, athletic data means data regarding or relating to a user's activity (or inactivity). In one embodiment, device 226 may wirelessly interact with a remote website such as a site dedicated to fitness or health related subject matter, either directly or indirectly (e.g., via a mobile device, such as device 138 associated with user 124). In this or another embodiment, device 226 may interact with a mobile device, such as device 138, as to an application dedicated to fitness or health related subject matter. In these or other embodiments, device 226 may interest with both a mobile device as to an application as above, such as device 138, and a remote website, such as a site dedicated to fitness or health related subject matter, either directly or indirectly (e.g., via the mobile device, such as device 138). In some embodiments, at some predetermined time(s), the user may wish to transfer data from the device 226 to another location. For example, a user may wish to upload data from a portable device with a relatively smaller memory to a larger device with a larger quantity of memory. Communication between device 226 and other devices may be done wirelessly and/or through wired mechanisms.

As shown in FIG. 2B, device 226 may include an input mechanism, such as a button 228, to assist in operation of the device 226. The button 228 may be a depressible input operably connected to a controller 230 and/or any other electronic components, such as one or more elements of the type(s) discussed in relation to computer 102 shown in FIG. 1B. Controller 230 may be embedded or otherwise part of housing 232. Housing 232 may be formed of one or more materials, including elastomeric components and comprise one or more displays, such as display 234. The display may be considered an illuminable portion of the device 226. The display 234 may include a series of individual lighting elements or light members such as LED lights 234 in an exemplary embodiment. The LED lights may be formed in an array and operably connected to the controller 230. Device 226 may include an indicator system 236, which may also be considered a portion or component of the overall display 234. It is understood that the indicator system 236 can operate and illuminate in conjunction with the display 234 (which may have pixel member 235) or completely separate from the display 234. The indicator system 236 may also include a plurality of additional lighting elements or light members 238, which may also take the form of LED lights in an exemplary embodiment. In certain embodiments, indicator system 236 may provide a visual indication of goals, such as by illuminating a portion of lighting members 238 to represent accomplishment towards one or more goals.

A fastening mechanism 240 can be unlatched wherein the device 226 can be positioned around a wrist of the user 124 and the fastening mechanism 240 can be subsequently placed in a latched position. The user can wear the device 226 at all times if desired. In one embodiment, fastening mechanism 240 may comprise an interface, including but not limited to a USB port, for operative interaction with computer 102 and/or devices 138, 140, and/or recharging an internal power source.

In certain embodiments, device 226 may comprise a sensor assembly (not shown in FIG. 2B). The sensor assembly may comprise a plurality of different sensors. In an example embodiment, the sensor assembly may comprise or permit operative connection to an accelerometer (including in the form of a multi-axis accelerometer), a gyroscope, a location-determining device (e.g., GPS), light sensor, temperature sensor (including ambient temperature and/or body temperature), heart rate monitor, image-capturing sensor, moisture sensor and/or combinations thereof. Detected movements or parameters from device's 142 sensor(s), may include (or be used to form) a variety of different parameters, metrics or physiological characteristics including but not limited to speed, distance, steps taken, and energy expenditure such as calories, heart rate and sweat detection. Such parameters may also be expressed in terms of activity points or currency earned by the user based on the activity of the user. Examples of wrist-worn sensors that may be utilized in accordance with various embodiments are disclosed in U.S. patent application Ser. No. 13/287,064, filed on Nov. 1, 2011, the contents of which are incorporated herein in their entirety for any and all non-limiting purposes.

II. Illustrative Monitoring Methods

System 100 may prompt a user to perform one or more exercises, monitor user movement while performing athletic movements (including a plurality of movements that comprise an exercise). Based upon the user's performance further instructions and/or feedback may be provided. In one embodiment, computer 102, image-capturing device 126, sensor 128, and display 136 may be implemented within the confines of a user's residence, although other locations, including schools, gyms and/or businesses are contemplated. Further, as discussed above, computer 102 may be a portable device, such as a cellular telephone; therefore, one or more aspects discussed herein may be conducted in almost any location.

A. Monitoring User Movements

Figure 3A:
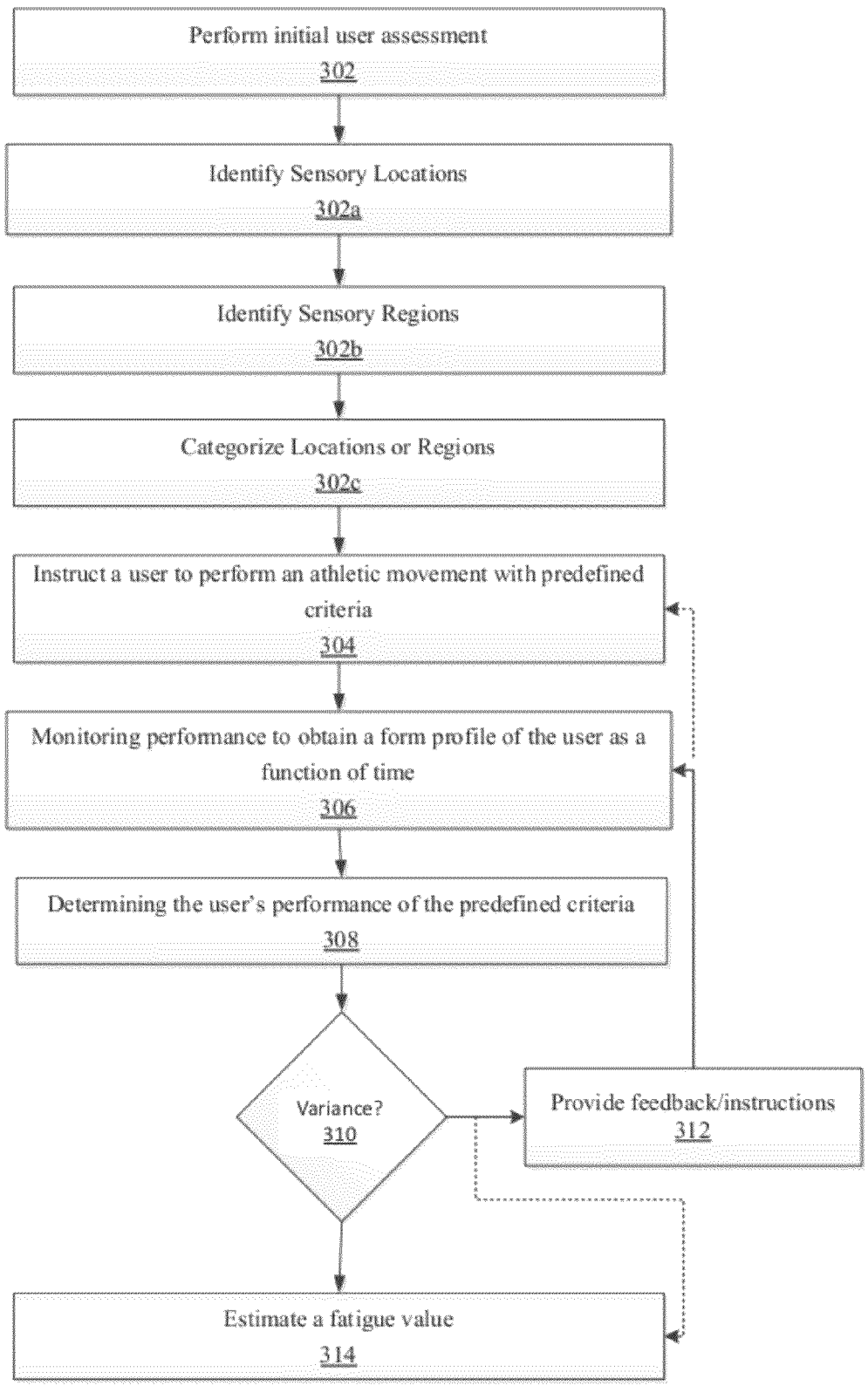
FIG. 3 illustrates an example flow diagram of a method for providing a user with feedback while exercising, in accordance with example embodiments.
Figure 3B:
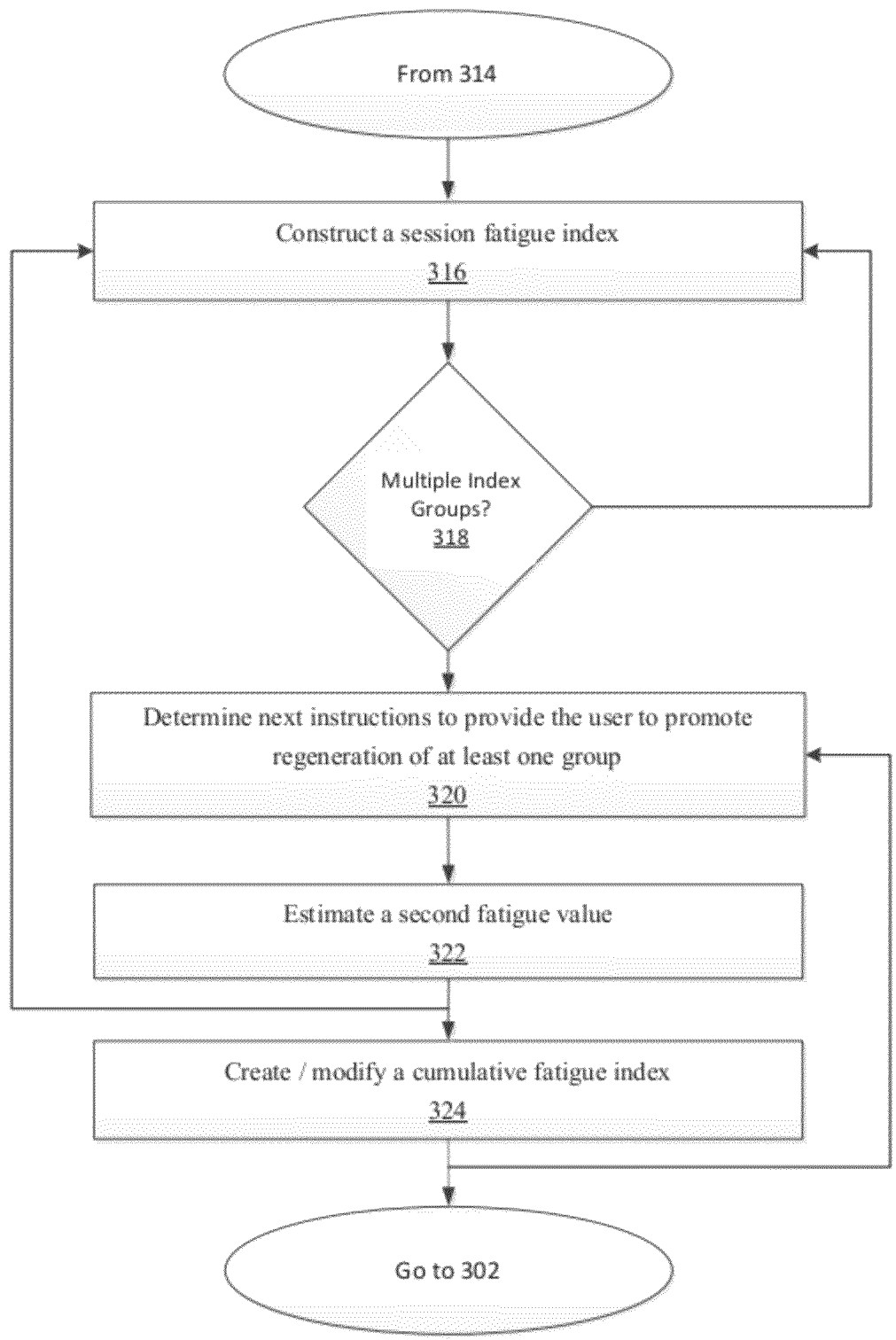

While exercising, the system 100 may use one or more techniques to monitor user movement. FIG. 3 illustrates an example flow diagram of a method for providing a user with feedback while exercising, in accordance with one or more example embodiments. The method may be implemented by a computer, such as, for example, computer 102, device 138, 140, 142 and/or 144, and/or other apparatuses. The blocks shown in FIG. 3 may be rearranged, some blocks may be removed, additional blocks may be added, each block may be repeated one or more times, and the flow diagram may be repeated one or more times. The flow diagram may begin at block 302.

1. Perform User Assessment

In block 302, one or more embodiments may include performing an initial assessment of the user. A user, such as user 124, may be positioned in range of a sensor, such as in front of the image capturing device 126 and/or sensor 128, which may comprise an infrared transceiver. Display 136 may present a representation of user 124 that may be a "mirror-image" or depict a virtual avatar, such as a user avatar, that moves to correspond with user movement. Computer 102 may prompt the user to move into a certain region relative to the image capturing device 126 and/or relative to the sensor 128 so that the user is within frame and/or range. When properly positioned, the system 100 may process movement of the user. Although the term "initial" has been utilized, this assessment may occur each time the user initiates system 100, or upon predetermined (e.g., regular or random) times that the user initiates system 100, or upon passage of time (e.g., from first initiation or thereafter based on such occurrences in turn), or each time the user performs any one or more of some predetermined, user-selected, sequence, set or other movement, or for any other reason. Thus, references to assessments herein are not limited to a single assessment.

a. Identify Sensory Locations

The system 100 may process sensory data to identify user movement data. In one embodiment, sensory locations may be identified (see block 302a). For example, images of recorded video, such as from image-capturing device 126, may be utilized in an identification of user movement. For example, the user may stand a certain distance, which may or may not be predefined, from the image-capturing device 126, and computer 102 may process the images to identify the user 124 within the video, for example, using disparity mapping techniques. In an example, the image capturing device 126 may be a stereo camera having two or more lenses that are spatially offset from one another and that simultaneously capture two or more images of the user. Computer 102 may process the two or more images taken at a same time instant to generate a disparity map for determining a location of certain parts of the user's body in each image (or at least some of the images) in the video using a coordinate system (e.g., Cartesian coordinates). The disparity map may indicate a difference between an image taken by each of the offset lenses.

Figure 4:
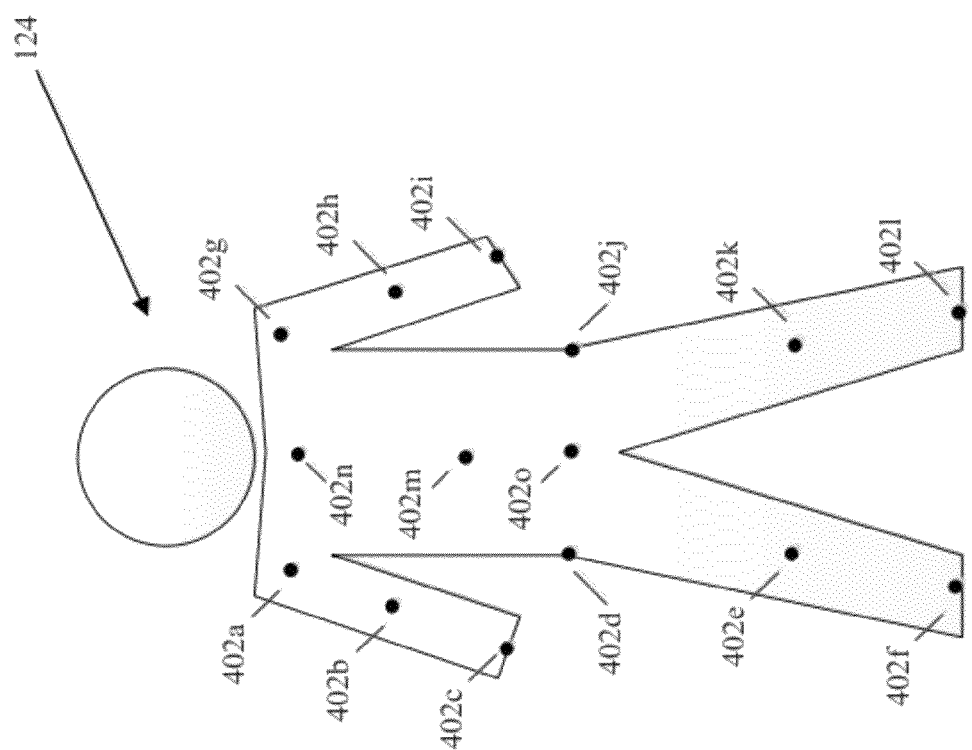
FIG. 4 illustrates example points on a user's body to monitor in accordance with example embodiments.

In a second example, one or more sensors may be located on or proximate to the user's 124 body at various locations or wear a suit having sensors situated at various locations. Yet, in other embodiments, sensor locations may be determined from other sensory devices, such as devices 138, 140, 142 and/or 144. With reference to FIG. 4, sensors may be placed (or associated with, such as with image-capturing device 126) body movement regions, such as joints (e.g., ankles, elbows, shoulders, etc.) or at other locations of interest on the user's 124 body. Example sensory locations are denoted in FIG. 4 by locations 402a-402o. In this regard, sensors may be physical sensors located on/in a user's clothing, yet in other embodiments, sensor locations 402a-402o may be based upon identification of relationships between two moving body parts. For example, sensor location 402a may be determined by identifying motions of user 124 with an image-capturing device, such as image-capturing device 126. Thus, in certain embodiments, a sensor may not physically be located at a specific location (such as sensor locations 402a-402o), but is configured to sense properties of that location, such as with image-capturing device 126. In this regard, the overall shape or portion of a user's body may permit identification of certain body parts. Regardless of whether an image-capturing device, such as camera 126, is utilized and/or a physical sensor located on the user 124, such as sensors within or separate from one or more of device(s) 138, 140, 142, 144 are utilized, the sensors may sense a current location of a body part and/or track movement of the body part. In one embodiment, location 402m may be utilized in a determination of the user's center of gravity (a.k.a., center of mass). For example, relationships between location 402a and location(s) 402f/402l with respect to one or more of location(s) 402m-402o may be utilized to determine if a user's center of gravity has been elevated along the vertical axis (such as during a jump) or if a user is attempting to "fake" a jump by bending and flexing their knees. In one embodiment, sensor location 402n may be located at about the sternum of user 124. Likewise, sensor location 402o may be located approximate to the naval of user 124. In certain embodiments, data from sensor locations 402m-402o may be utilized (alone or in combination with other data) to determine the center of gravity for user 124. In further embodiments, relationships between multiple several sensor locations, such as sensors 402m-402o, may be utilized in determining orientation of the user 124 and/or rotational forces, such as twisting of user's 124 torso. Further, one or more locations, such as location(s), may be utilized to as a center of moment location. For example, in one embodiment, one or more of location(s) 402m-402o may serve as a point for a center of moment location of user 124. In another embodiment, one or more locations may serve as a center of moment of specific body parts or regions.

In certain embodiments, a time stamp to the data collected (such as collected part of block 302 in FIG. 3) indicating a specific time when a body part was at a certain location. Sensor data may be received at computer 102 (or other device) via wireless or wired transmission. A computer, such as computer 102 and/or devices 138, 140, 142, 144 may process the time stamps to determine the locations of the body parts using a coordinate system (e.g., Cartesian coordinates) within each (or at least some) of the images in the video. Data received from image-capturing device 126 may be corrected, modified, and/or combined with data received from one or more other devices 138, 140, 142 and 144.

In a third example, computer 102 may use infrared pattern recognition to detect user movement and locations of body parts of the user 124. For example, the sensor 128 may include an infrared transceiver, which may be part of image-capturing device 126, or another device, that may emit an infrared signal to illuminate the user's 124 body using infrared signals. The infrared transceiver 128 may capture a reflection of the infrared signal from the body of user 124. Based on the reflection, computer 102 may identify a location of certain parts of the user's body using a coordinate system (e.g., Cartesian coordinates) at particular instances in time. Which and how body parts are identified may be predetermined based on a type of exercise a user is requested to perform.

Figure 5:
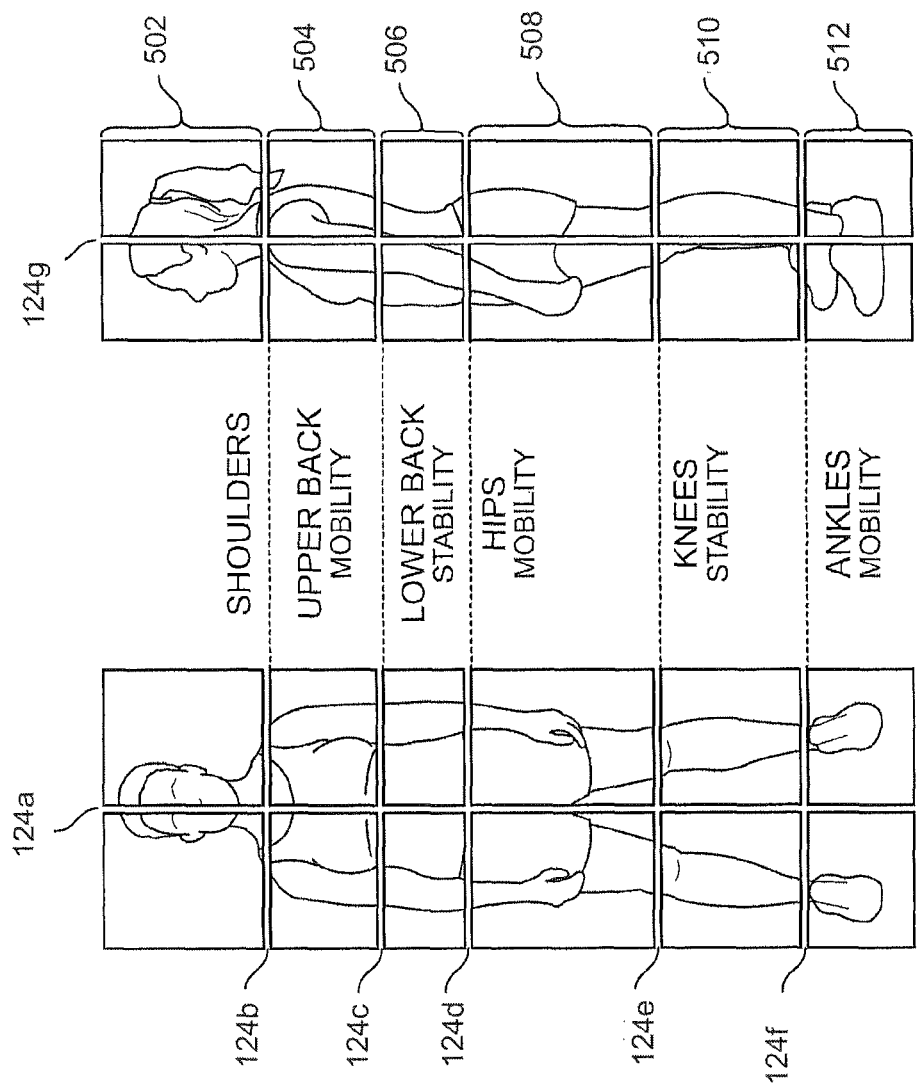
FIG. 5 illustrates an example posture assessment in accordance with example embodiments.

As part of a workout routine, computer 102 may make an initial postural assessment of the user 124 as part of the initial user assessment in block 302 of FIG. 3. With reference to FIG. 5, computer 102 may analyze front and side images of a user 124 to determine a location of one or more of a user's shoulders, upper back, lower back, hips, knees, and ankles. On-body sensors and/or infrared techniques may also be used, either alone or in conjunction with image-capturing device 126, to determine the locations of various body parts for the postural assessment. For example, computer 102 may determine assessment lines 124a-g to determine the locations of a various points on a user's body, such as, for example, ankles, knees, hips, upper back, lower back, and shoulders.

b. Identify Sensory Regions

In further embodiments, system 100 may identify sensor regions (see, e.g. block 302b). In one embodiment, assessments lines 124a-g may be utilized to divide the user's body into regions. For example, lines 124b-f may be horizontal axes. For example, a "shoulders" region 502 may correlate to a body portion having a lower boundary around the user's shoulders (see line 124b), region 504 may correlate to the body portion between the shoulders (line 124b) and about half the distance to the hips (see line 124c) and thus be an "upper back" region, and region 506 may span the area between line 124c to the hips (see line 124d) to comprise a "lower back region." Similarly, region 508 may span the area between the "hips" (line 124d) and the "knees" (see line 124e), region 510 may span between lines 124e and 124f and region 512 (see "ankles") may have an upper boundary around line 124f. Regions 502-512 may be further divided, such as into quadrants, such as by using axes 124a and 124g.

c. Categorize Locations or Regions

Regardless of whether specific points (e.g., locations shown in FIG. 4) and/or regions (e.g. regions shown in FIG. 5), body parts or regions that are not proximate to each other may nonetheless be categorized into the same movement category (see, e.g. block 302c). For example, as shown in FIG. 5, the "upper back", "hips", and "ankles" regions 504, 508, 512 may be categorized as belonging to a "mobility" category. In another embodiment, the "lower back" and "knees" regions 506, 510 may be categorized as belonging to a "stability" category. The categorizations are merely examples, and in other embodiments, a location or region may belong to multiple categories. For example, a "center of gravity" region may be formed from regions 504 and 506. In one embodiment, a "center of gravity" may comprise portions of regions 504 and 506. IN another embodiment, a "center of moment" category may be provided, either independently, or alternatively, as comprising a portion of at least another category. In one embodiment, a single location may be weighted in two or more categories, such as being 10% weighted in a "stability" category and 90% weighted in a "mobility" category.

Computer 102 may also process the image to determine a color of clothing of the user or other distinguishing features to differentiate the user from their surroundings. After processing, computer 102 may identify a location of multiple points on the user's body and track locations of those points, such as locations 402 in FIG. 4. Computer 102 may also prompt the user to answer questions to supplement the postural assessment, such as, for example, age, weight, etc. Again, each of 302a-302c (as well as the entirety) of 302 is optional and is not required in accordance with various embodiments.

2. Providing Instructions

With reference again to FIG. 3, in block 304, one or more embodiments may instruct a user to perform an athletic movement with predefined criteria. In certain embodiments, block 304 may include prompting a first user, such as user 124, to perform at least one exercise during a workout session. In an example, system 100 may prompt a user to perform one or more exercises during a workout session. A workout session may include a predetermined number of exercises (e.g., push-ups, squats, lunges, etc.) where computer 102 prompts the user to perform a predetermined number of repetitions of each exercise. A workout session may also involve a single athletic activity (e.g., run 10 miles).

Instructions to user 124 may be audible, visual, tactile or combinations thereof. Block 304 may include demonstrating proper form for an exercise and prompting the user to perform the exercise. In certain embodiments, at least a portion of the instructions may relate to a personalized workout program. In one embodiment, a personalized workout program may be formed, at least in part, from data collected as part of block 302. Further, data collected from one or more other devices, such as devices 138, 140 and, or 142, may be utilized in determining which instructions to provide and/or how to provide instructions to the user 124.

Figure 6:
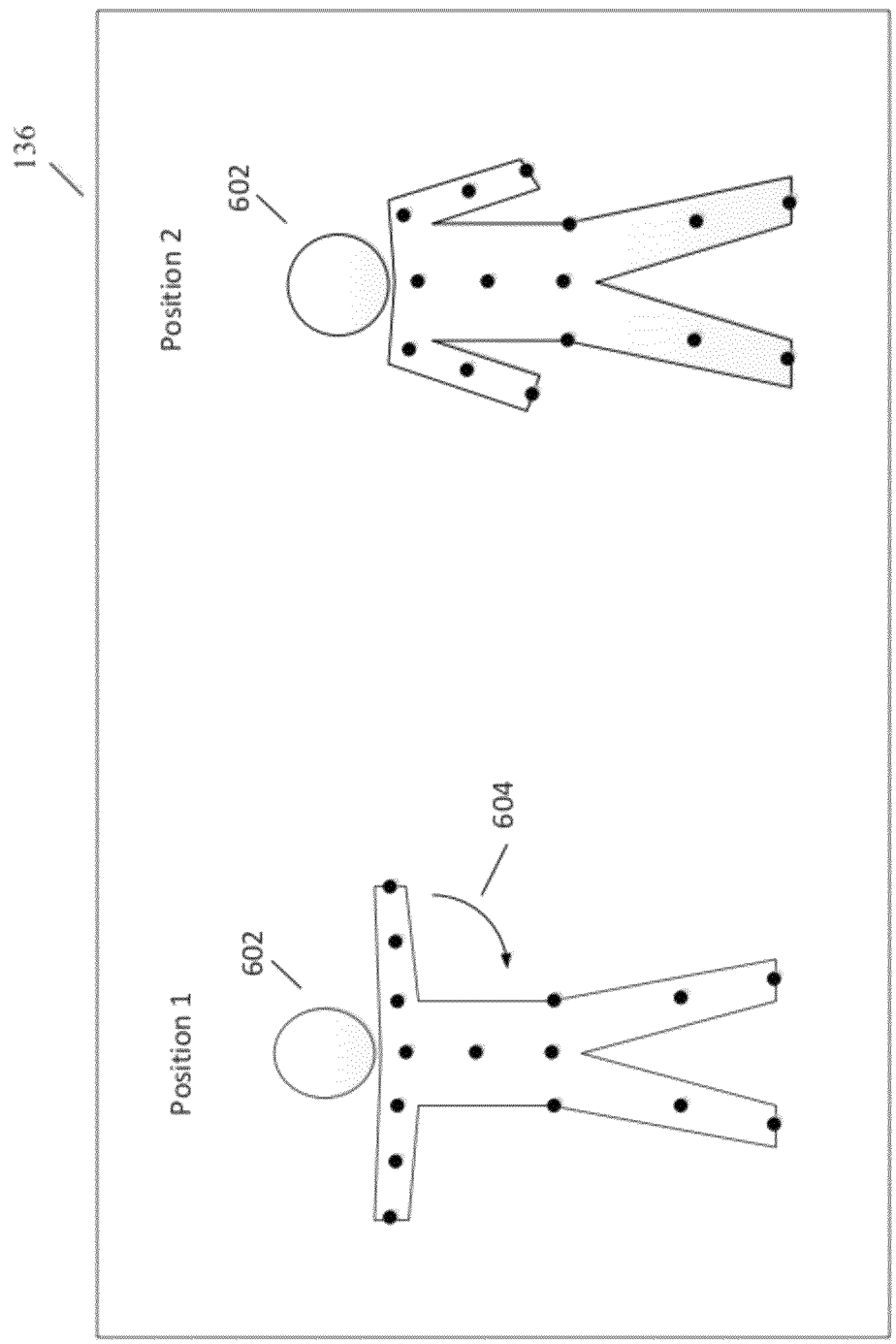
FIGS. 6-7 illustrate example displays of a virtual trainer instructing a user on how to perform an exercise in accordance with example embodiments.
Figure 7:
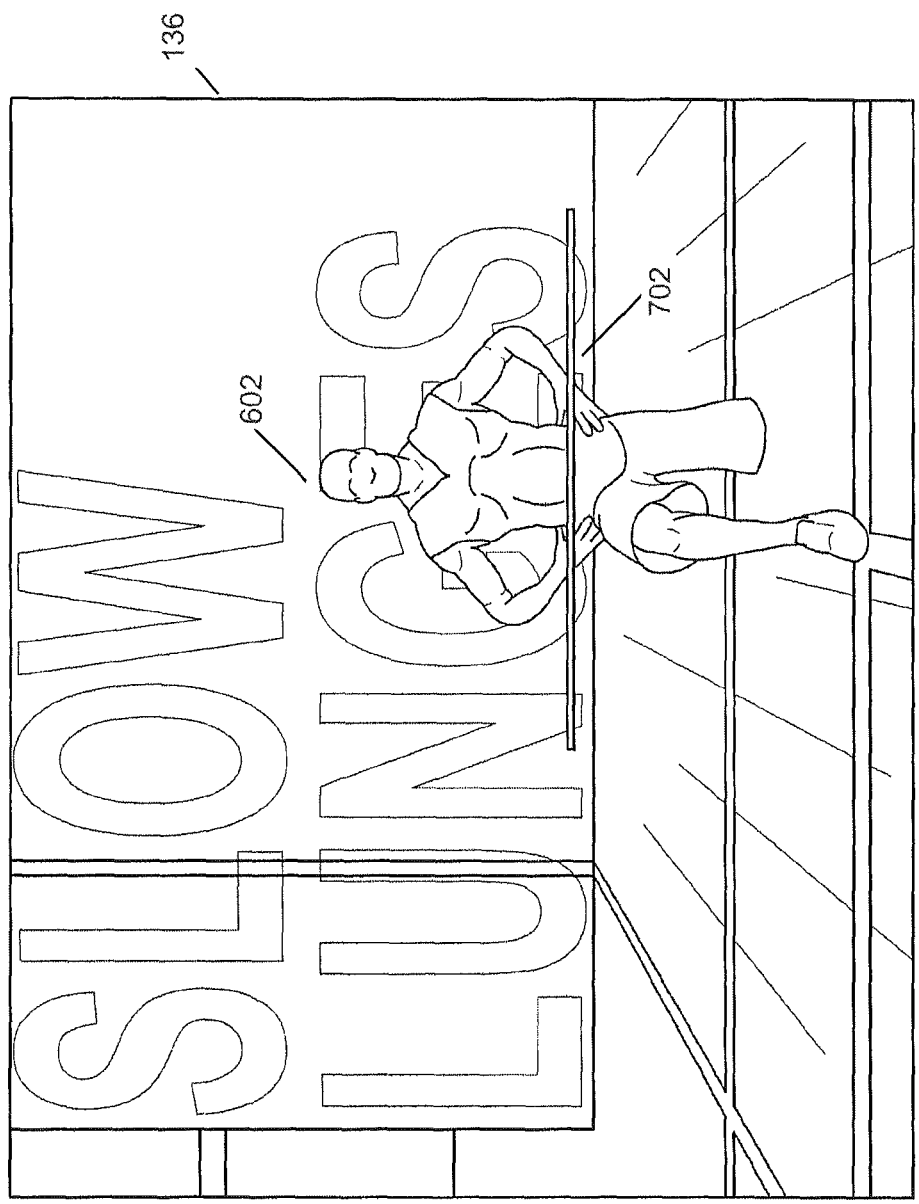

In accordance with certain implementations, system 100 may cause the display 136 to present a virtual trainer demonstrating an exercise to instruct the user on proper form. FIGS. 6-7 illustrate example displays of a virtual trainer 602 performing an exercise in accordance with example embodiments. With reference to FIG. 6, the display 136 may present a virtual trainer 602 at multiple positions (e.g., switching from "Position 1" to "Position 2") as well as an arrow 604 instructing a user in which direction to move. With reference to FIG. 7, the display 136 may present an animation of the virtual trainer 602 demonstrating proper form for performing a repetition of an exercise (e.g., a slow lunge).

In addition to or instead of a virtual trainer, such as trainer 602, the display 136 may present a depiction and/or an actual video of a real person demonstrating proper form for an exercise. Any graphical or video instructions may be accompanied by audio and/or tactile instructions. Instructions may include form guidance information, such as form guidance information 702 (shown in FIG. 7), which may be presented on the virtual trainer 602 when demonstrating an exercise. Form guidance information 702 may be a straight line, an angle between lines, or other information to guide the user about proper form for an exercise. In FIG. 7, for instance, form guidance information 702 is a straight line across a user's hip bones instructing the user to keep their hips level relative to the floor. Form guidance information may be provided through feedback mechanisms that do not include graphical or textual data overlaid on an avatar, such as virtual trainer 602. In this regard, form guidance information may include audio or tactile information, including but not limited to the examples described herein.

Figure 8:
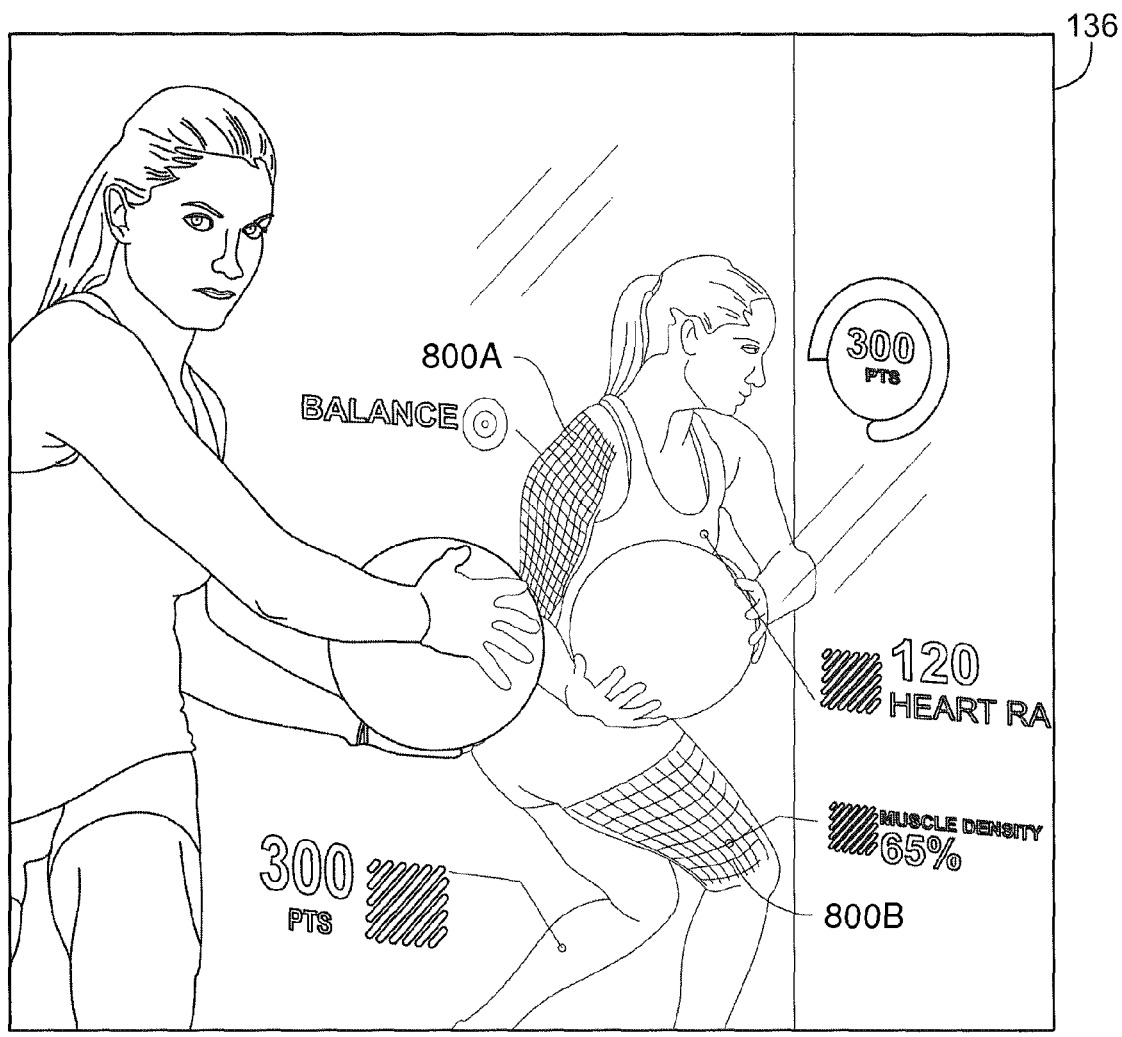
FIG. 8 illustrates an example of onion skinning on an image of a user in accordance with example embodiments.

In accordance with further implementations, instructions may target a specific group (or a plurality of groups) of body systems, such as muscle groups. For example, display 136 may convey the body systems targeted during athletic activities, such as muscle groups targeted during an exercise. FIG. 8 illustrates an example graphical display providing a user with feedback on muscles being developed by an exercise in accordance with example embodiments. In one embodiment, system 100 may process an image of the user 124 and cause the display 136 to present a grid 800A/800B on one or more muscles being developed by an exercise. As seen in FIG. 8, a grid 800A is displayed proximate to a user's shoulder and arm, and grid 800B is displayed proximate to a user's hamstring. Displaying a grid on a user's muscle or muscle group may be referred to as "onion-skinning." Onion skinning may be used to focus a user's attention on a particular system or region, such as a muscle or muscle group worked during an exercise. System 100 may also cause the display 136 to present onion skinning on a virtual trainer avatar (such as trainer 602 shown in FIG. 6) during demonstration of an exercise. After or during a workout, the user 124 may select the onion skinned location using a computer mouse or other input device, by making a motion in front of the image capturing device 126, or by a voice command to instruct computer 102, to peel back the avatar's skin to display the muscle working during the exercise.

B. Monitoring User Performance

One or more embodiments may comprise monitoring a user performing the movement (or exercise) instructed in block 304 (see, e.g., block 306). Monitoring may comprise obtaining and/or deriving data from one or more of the sensors described above in reference to block 302, including devices 138, 140 and/or 142, computer 102, sensors 126, 128, network 132, and/or comprise any one or more of sensor locations shown in FIG. 4. In one embodiment, sensors may sense a current location of a body part and/or track movement of the body part.

Various embodiments may determine the user's performance of the predefined criteria (see, e.g., block 308). In one embodiment, sensor data may be utilized, alone or in combination with other data, to determine the user's performance. In one embodiment, sensor data may be obtained from one or more of the sensors utilized in block 306 or and/other processes that may monitor the user's performance. Further, as discussed below, data obtained from other activities, such as a prior workout performed at one or more different locations may be utilized. As one example, a user may have conducted a run earlier that day. For example, a shoe sensor and/or a mobile device, such as a mobile telephone with a location-determining sensor (such as, for example, GPS), may have collected data regarding the user's run. Such data may be utilized in the determination of whether the user (or groups, regions, and/or systems of the user) may be fatigued.

Further embodiments may utilize one or more inputs from the user. In certain embodiments, at least one input is not a direct physiologic parameter based upon the user's performance of the instructed movement. In one embodiment, one or more input may comprise information relating to a user's reaction to inquiries and/or stimuli differing from the instructions to perform the initial movement (e.g. see block 304). As an example, system 100 may provide user 124 an opportunity to take a "rest" or recovery following a drill. Responses by the user 124 may be utilized in determining aspects of their performance. For example, different scores and/or weights may be provided based on for example, 1) whether the user took a recovery period; 2) the length of the recovery period; 3) their actions during any recovery period, and/or 4) combinations thereof. Other implementations may include, for example, asking user 124 to rate the difficulty of the instructed performance, their perceived performance, whether, and if so, when they would like to do it again, and/or any other criteria. In further embodiments, based upon the user's feedback, system 100 may store values relating to the user's abilities and preferred level of exertion (in addition to and/or separate from fatigue determinations).

In a further embodiment, the first instructions (such as provided during block 304) may instruct the user to perform a specific drill, and block 308 (and/or other processes, including for example, 310 and/or 312, which are discussed below) may utilize not only measurements regarding performance of the drill, but also one or more of: 1) activities of user 124 before the instructed performance; 2) activities of user 124 following the instructed performance; and/or 3) feedback from the user as discussed above, which may occur before, during and/or after the user 124 performs the instructed movement(s).

In further embodiments, determinations relating to the user's performance may be based (either entirely or partially) upon the user's feedback. For example, during and/or following the performance of the instructed movement(s), user 124 may be provided with an opportunity to rate certain aspects of their performance. In one embodiment, user 124 may rate one or more subjective criteria, such as for example: difficulty, subjective fatigue, soreness or pain, enjoyment, and combinations thereof. In certain implementations this may be advantageous to consider a user's preferred exertion and perceived exertion rather than a measured exertion. In further embodiments, one or more of fatigue, abilities, preferred level of exertion, and/or other criteria be utilized to determine enhance performance over time and/or systems and methods to improve performance over time. In yet further embodiments, one or more of abilities, preferred level of exertion, and/or enhanced performance over time may be utilized to determine fatigue and/or utilized to improve measurements of fatigue. Those skilled in the art with the benefit of this disclosure will appreciate that these are merely examples, and that other criteria, inclusive of the ones listed, may be utilized.

1. Example Form Profile

Monitoring of user's 124 performance may comprise obtaining a form profile of user 124, or a portion thereof, as a function of time. Monitoring of the user (as well as determinations of the user's performance) may be performed on a real-time basis. As an example, computer 102 may cause a display, such as display 136, to present a user representation with real-time feedback. System 100 may process captured data, such as from the images, infrared data, and/or sensor data, to determine a relationship between certain body parts. These relationships may include an angle of one body part relative to another. For example, when the user is doing a squat, computer 102 may compare an angle formed between a user's torso and thigh. In another example, computer 102 may compare a location of a user's shoulder relative to their elbow and hand during a push up. In another example, computer 102 may compare shoulders and hips to determine relative rotation there between, and/or either or both shoulder and hips relative to one or more feet to determine relative rotation there between or there among, and/or absolute rotation of either the hips or shoulders. Angles, rotations, and other relationships between or among any one or more desired body part(s) may be monitored and analyzed. Angles, rotations, and other relationships between or among a reference point (e.g., off body) and any one or more desired body part(s) may be monitored and analyzed.

Figure 9:
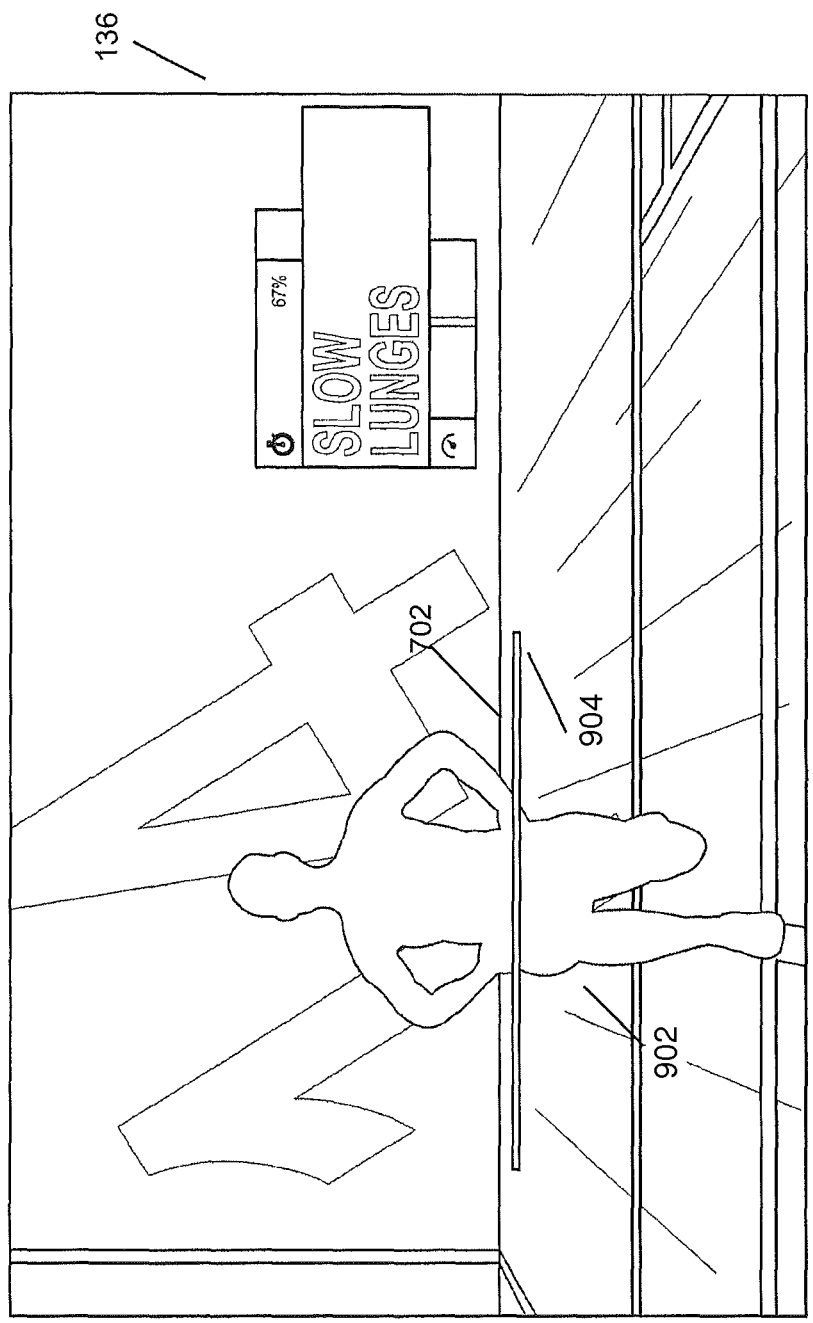
FIG. 9 illustrates example displays of a user avatar performing an exercise in accordance with example embodiments.

FIG. 9 illustrates an example display of a user representation performing an exercise in accordance with example embodiments, however, other graphical representations, such as those shown in FIG. 7 may be utilized. For example, voices or sounds may provide an indication of how straight a user's hips are (or are not). In another embodiment, a signal may be provided to a device, such as sensor device(s) 138, 140, 142 and/or 144 to provide vibrational output configured to be felt by user 124 to provide guidance. For example, a vibration may be provided to the sensor device 138 upon determining that the user's hips are not straight. Feedback may be based on monitoring the user 124 during performance of the movement, such as that described below in relation to block 312.

While user 124 is performing movements, computer 102 may create a user representation for display by the display 136. The computer 102 may create the user representation based on one or more of processing some or all images of video captured by image capturing device 126, processing data received from the sensor 128, and processing data received from sensors 138, 140, 142, and 144. The user representation may be, for example, video of the user, or a user avatar 802 created based on image and/or sensor data, including infrared data. To assist the user 124, display 136 may also present form guidance information 702 on user avatar 902, as well as current form information 904 for the user (See, FIG. 9). Current form information 904 may be a measurement of a user's current form of interest in a particular exercise. Current form information 904 may be a straight line between particular body parts, an angle between certain body parts, curvature of a body part, or other information being monitored for a particular exercise. For example, as seen in FIG. 9, current form information 904 may be a straight line between a user's hips to indicate if one hip sags relative to the other (e.g., to indicate whether a straight line between the user's hips is parallel with the floor). Also, the user may place sensors on their body at their hip bones, or computer 102 may estimate a location of a user's hip bones based on detected infrared information.

Further, with reference again to FIG. 4, location of user's 124 body and/or body parts may be utilized in monitoring and determining performance. As an example, location 402m may be utilized in a determination of the user's center of gravity (a.k.a, center of mass). For example, relationships between location 402a and location(s) 402f/402l with respect to one or more of location(s) 402m-402o may be utilized to determine if a user's center of gravity has been elevated along the vertical axis (such as during a jump) or if a user is attempting to "fake" a jump by bending and flexing their knees. Likewise, sensor location 402o may be located proximate to the naval of user 124. In certain embodiments, data from sensor locations 402m-402o may be utilized (alone or in combination with other data) to determine the center of gravity for user 124. In further embodiments, relationships between multiple several sensor locations, such as sensors 402m-402o, may be utilized in determining orientation of the user 124 and/or rotational forces, such as twisting of user's 124 torso. Further, one or more locations may be utilized to as a center of moment location. For example, in one embodiment, one or more of location(s) 402m-402o may serve as a point for a center of moment location of user 124. In another embodiment, one or more locations may serve as a center of moment of specific body parts or regions.

Figure 10B:
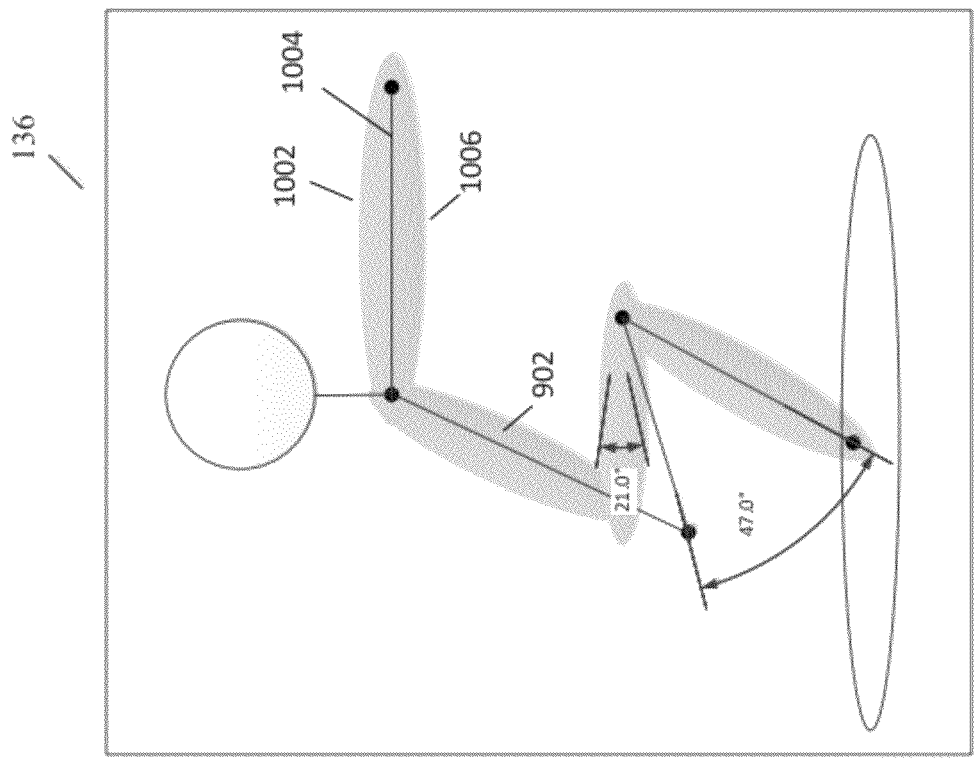
FIGS. 10A-10B illustrate example displays for depicting a user avatar relative to a virtual shadow for detecting improper form and providing feedback to a user in accordance with example embodiments.
Figure 10A:
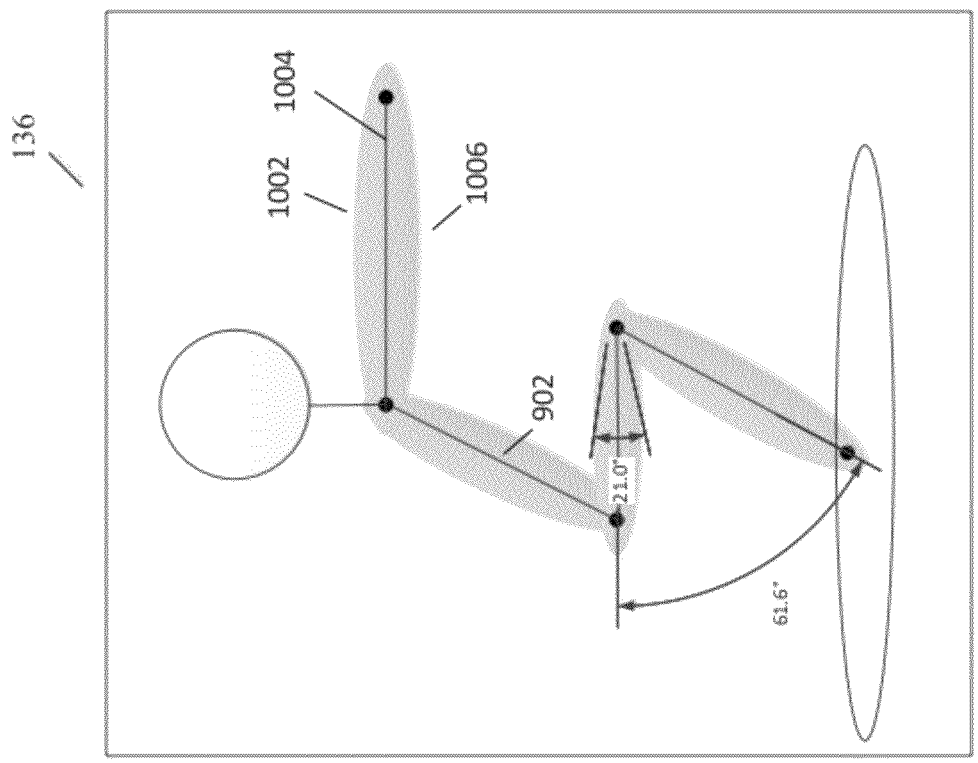

Shapes that virtually represent user 124, and/or the user's movements, may be utilized in monitoring any performance(s). In certain embodiments, a user shadow and/or user avatar may be utilized. In FIG. 10A a user avatar 902 may be represented by one or more lines, such as including line 1004. Line(s) 1004 may be positioned within a shadow, such as shadow 1006, which may have be indicated by perimeter 1002. System 100 may monitor the user's form and look for certain angles between a user's body parts, as well as determining whether the user avatar 902 remains within the shadow's 1006 perimeter 1002. For example, the system 100 may monitor an angle between the thigh and shin of the user avatar 902, as well as an angle between a user's torso and thighs. In an example, a desired angle between a user's thigh and shin may be 61.6°, and acceptable form may be within a range of 21° of the desired angle (e.g., between 50.5° and 72.1°). In FIG. 10B, an angle between the thigh and shin of the user avatar 902 may fall outside of the desired range (e.g., 47°).

In certain embodiments, a time stamp may be associated with at least a portion of data collected (such as collected part of block 306 in FIG. 3). In certain embodiments, a time stamp may indicate a time reference when a body part was at a certain location. Sensor data may be received at computer 102 (or other device) via wireless or wired transmission. A computer, such as computer 102 and/or devices sensors 138, 140, 142, 144 may process the time stamps to determine the locations of the body parts using a coordinate system (e.g., Cartesian coordinates) within each (or at least some) of the images in the video. Data received from image-capturing device 126 may be corrected, modified, and/or combined with data received from one or more other devices 138, 140, and 142.

2. Variance from Predefined Criteria

Various embodiments may determine whether user's 124 performances of the predefined criteria fail to meet a threshold or otherwise varies from at least one parameter relating to the predefined criteria (see, block 310). In one embodiment, any device within system 100 may compare captured data to desired data for an exercise (which may be a series of athletic movements) to monitor the user's form while performing an exercise. The desired data may include multiple comparison points throughout an exercise, and/or locations of various body parts during the exercise. For example, a push up may be divided into four events: (1) the lowest point where the user's 124 chest is nearest to the ground or other reference point and/or their arms are bent at a maximum bend; (2) a highest point where the user's 124 chest is farthest from the ground and/or their arms are straightened (e.g., a maximum straightness); (3) an upward event where the user transitions from the lowest point to the highest point; and (4) a downward event where the user transitions from the highest point to the lowest point.

The desired data may specify comparison points for each of these events focusing on certain body parts. For example, at each comparison point during a pushup, any component (or combination thereof) of system 100 may monitor the spacing of the user's hands, the straightness of the user's back, a location of the user's head relative to their torso, the spacing of the user's feet relative to one another, and/or other aspects. The desired data may specify desired locations for each body part being monitored during comparison points for an exercise, as well as permitted variations from the desired locations.

C. Feedback/Instructions Based Upon Variance

Optionally, system 100 may provide feedback and/or instructions to user 124 (see decision 310 and block 312 of FIG. 3) if the user and/or the user's body part varies beyond what is permitted for the predefined criteria. In one embodiment, the instructions may comprise at least a portion of the instructions provided at block 304. In another embodiment, instructions (whether audio, visual, tactile or combinations thereof) may provide encouragement and/or motivation to user 124 to complete the criteria, or to improve on an aspect of their performance of a criterion. For example, if user 124 is underperforming on a pushup, system 100 may indicate what the user's deficiency is, and/or provide feedback on how to improve or correct that deficiency. In one embodiment, system 100 may provide the user 124 with feedback identifying the body part and a correction to the user's form (e.g., back is arched, and not straight, during a pushup). System 100 may monitor each deficiency as a function of time. Thus, it may provide different feedback based upon the level of deficiency and/or rate of degradation of form. In certain embodiments, a high variation or determination that the user may be in pain may result in stopping the exercise or athletic movement being instructed.

In further embodiments, the instructions/feedback may prompt the user to try harder, keep going, or otherwise encourage meeting a goal or a predefined criterion of the movement or exercise. System 100 may allow a period of time to elapse between one or more instructions/feedback, which may be different from each other. In one embodiment, a first feedback may be provided to indicate a body part or region is outside of a compliance zone or otherwise not meeting a threshold. Upon user 124 not correcting the deficiency within an elapsed period of time, a second feedback may be provided. The second feedback may further indicate that the body part or region is outside of a compliance zone or otherwise not meeting a threshold. Yet, in other embodiments, the second feedback may provide encouragement. For example, system 100 may encourage the user to try harder or keep going. The motivation may be general, such as to keep trying or encouraging user 124 to give it all their effort. Yet, in other embodiments, system 100 may push the user harder and/or increase the difficulty of at least one criterion of the movement. For example, the threshold level for at least one parameter may be adjusted. In another embodiment, a time period required for completion and/or a tempo of a movement may be adjusted to increase or decrease the difficulty of the exercise. In one embodiment, the difficulty may be decreased and/or the user may be provided advice to "cool down" or otherwise notified that the difficulty of at least one parameter has been adjusted. System 100 may provide feedback to correct one problem at a time, and certain problems may take priority over others. Certain exercises or movements may place a user at risk for injury if not performed properly. Improper form that may result in injury may be of the highest priority, and from there other improper body part locations may be prioritized to assist the user in obtaining the full benefit of the exercise.

As part of the overlap determinations and/or other criteria, system 100 may cause the display 136 to present a recommended correction to the user's form. This may be performed whether there is an indication of either an acceptable form zone or an unacceptable form zone. With reference to FIG. 10B, the conveyed instruction/feedback may be provided to prompt the user to straighten their knees. Computer 102 may also cause the displayed video of the user avatar 902 to flash a color, to highlight a particular body part in color, to sound a tone or provide an audible instruction (e.g., straighten your back), to zoom in on or enlarge video of a body part or region of a user's body that has poor form, display a chart illustrating a difference between measured and desired form (e.g., angle between upper arm and form is 25% greater than desired), or other manners to audibly or visually inform the user of the problem. Although the correction is shown as part of avatar 902, other embodiments may show corrections as part of a shadow.

When in the unacceptable form zone, computer 102 may provide feedback identifying misplaced body parts attempting to improve the user's form to move into the acceptable form zone. Once in the acceptable form zone, computer 102 may provide feedback identifying misplaced body parts attempting to improve the user's form to move into the good form zone. If the user's form continues to be in the unacceptable form zone after a predetermined number of repetitions, computer 102 may stop the exercise or routine. In certain embodiments, system 100 may inform the user of the error and/or demonstrate the exercise again. Computer 102 may also change the exercise to an easier one or may adapt the repetitions based on a user's execution. As the user's form improves over time, computer 102 may shift from providing corrective feedback (e.g., instruction and correction) to providing motivation.

FIGS. 10A-B illustrate example displays for depicting a user avatar 902 relative to a virtual shadow 1006 for detecting improper form and providing feedback to a user 124 in accordance with example embodiments. As discussed above in relation to FIG. 10B, an angle between the thigh and shin of the user avatar 902 may fall outside of the desired range (e.g., 47°). Thus, in one embodiment, avatar 902 may be displayed as not being completely within the shadow 1006 to emphasize that the user (represented by avatar 902) has improper form. For example, as seen in FIG. 10B, the thigh of the user avatar 902 is outside of the thigh of the shadow perimeter 1002. For example, shadow 1006 may be defined with an area having an outer perimeter, such as the perimeter 1002. Although perimeter 1002 of shadow 1006 is shown as a single perimeter, those skilled in the art with the benefit of this disclosure will understand that shadow 1006 may be comprised of multiple sections or regions, each with their own respective perimeter. Also, the problem area may be highlighted in the display 136 with an instruction to improve the user's form. For example, the display 136 may present an instruction that instructs the user to maintain their thighs parallel to the ground at the lowest point of a squat. Data received from multiple sensors, which may be variously disposed (including on the user) may be utilized in these and other determinations.

Figure 11:
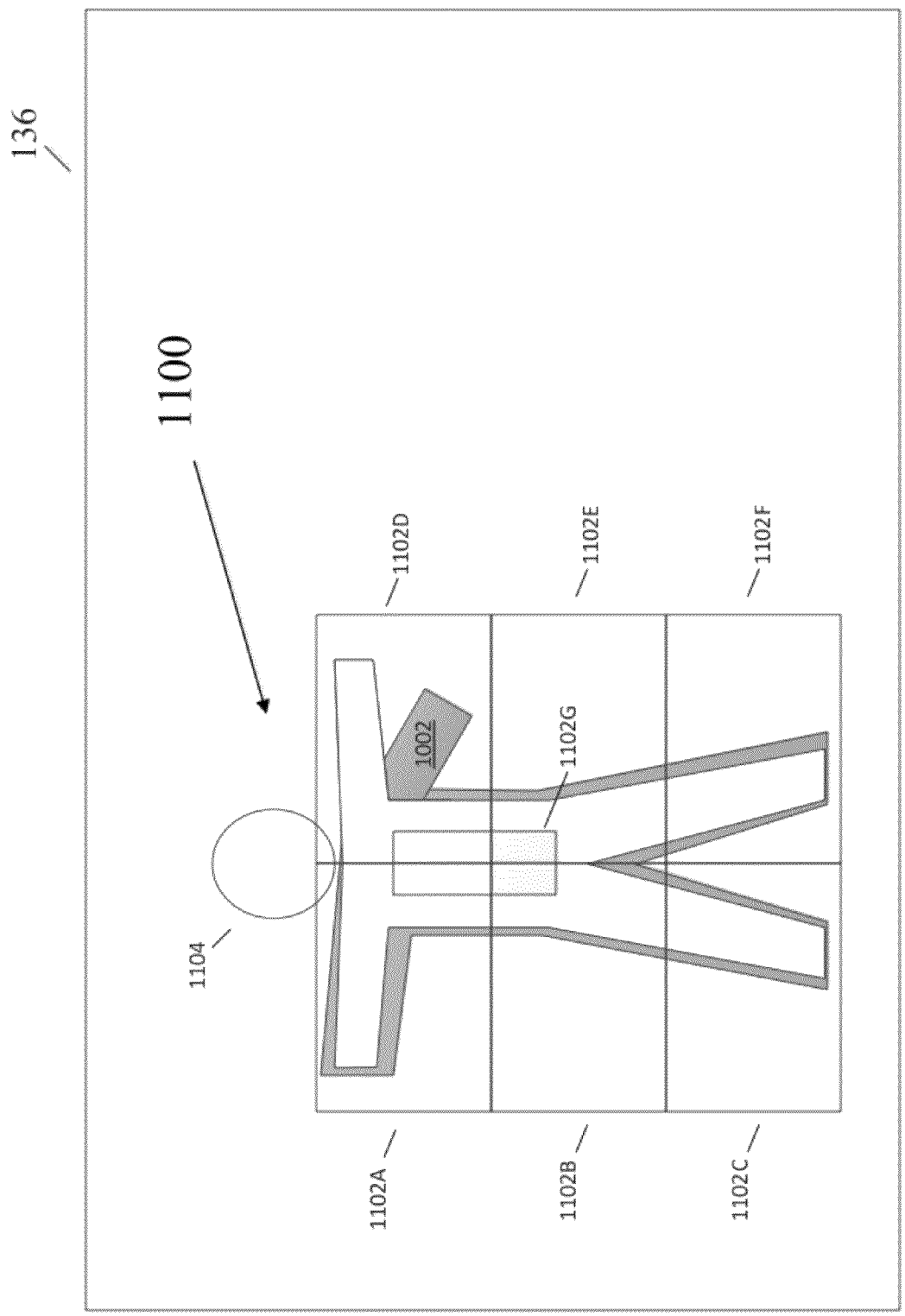
FIG. 11 illustrates an example display of image subsections showing an amount of overlap between a user avatar and a virtual shadow in accordance with example embodiments.

Feedback may concentrate on a specific deficiency and/or area of user's body. In one embodiment, computer 102 (or any other electronic device) may divide an image from captured video into subsections to identify body parts that may be performing an incorrect movement, as shown in FIG. 11. In other embodiments, the sub-sections may be the similar to the regions discussed in relation to FIG. 5.

Looking to FIG. 11, computer 102 may divide sensed data, represented by image 1100, into unique subsections 1102 and may determine the amount of overlap between a shadow, which may be shadow 1006 (as also shown in FIG. 10), and the user avatar 1104 in each subsection. In one embodiment, one or more subsections 1102A-G may correspond to quadrants, such as the quadrants illustrated in FIG. 5. In an example, FIG. 11 shows six different subsections 1402A-F; however, any desired number may be used. Computer 102 may compare the overlap to identify a subsection having a lowest percentage of overlap (e.g., subsection 1102D in FIG. 11). Computer 102 also may identify one or more subsections having a percentage overlap below a predetermined amount (e.g., less than 60%).

In other examples, computer 102 may determine an amount of overlap by processing the infrared data and/or the sensor data to determine locations, of a user's body parts (such as for example, one or more of locations 402a-m), and comparing the identified locations to desired locations. Computer 102 may define overlap zones that compare the amount of distance between a desired body part location and an actual location. For example, a good form zone may be within a first distance from a desired location (e.g., elbow is within 2 inches from desired location) or vary by no more than a certain percentage (e.g., 5%) from the desired location. An acceptable form zone may be within a second distance range of a desired location (e.g., elbow is within 2-4 inches from desired location) or where a body part differs by no more than a certain percentage (e.g., 15%) from the desired location. An unacceptable form zone may be more than a certain distance away from a desired location and/or where a body part differs by more than a certain percentage (e.g., more than 15%) from a desired location. Any number of zones may be defined.

Figure 12:
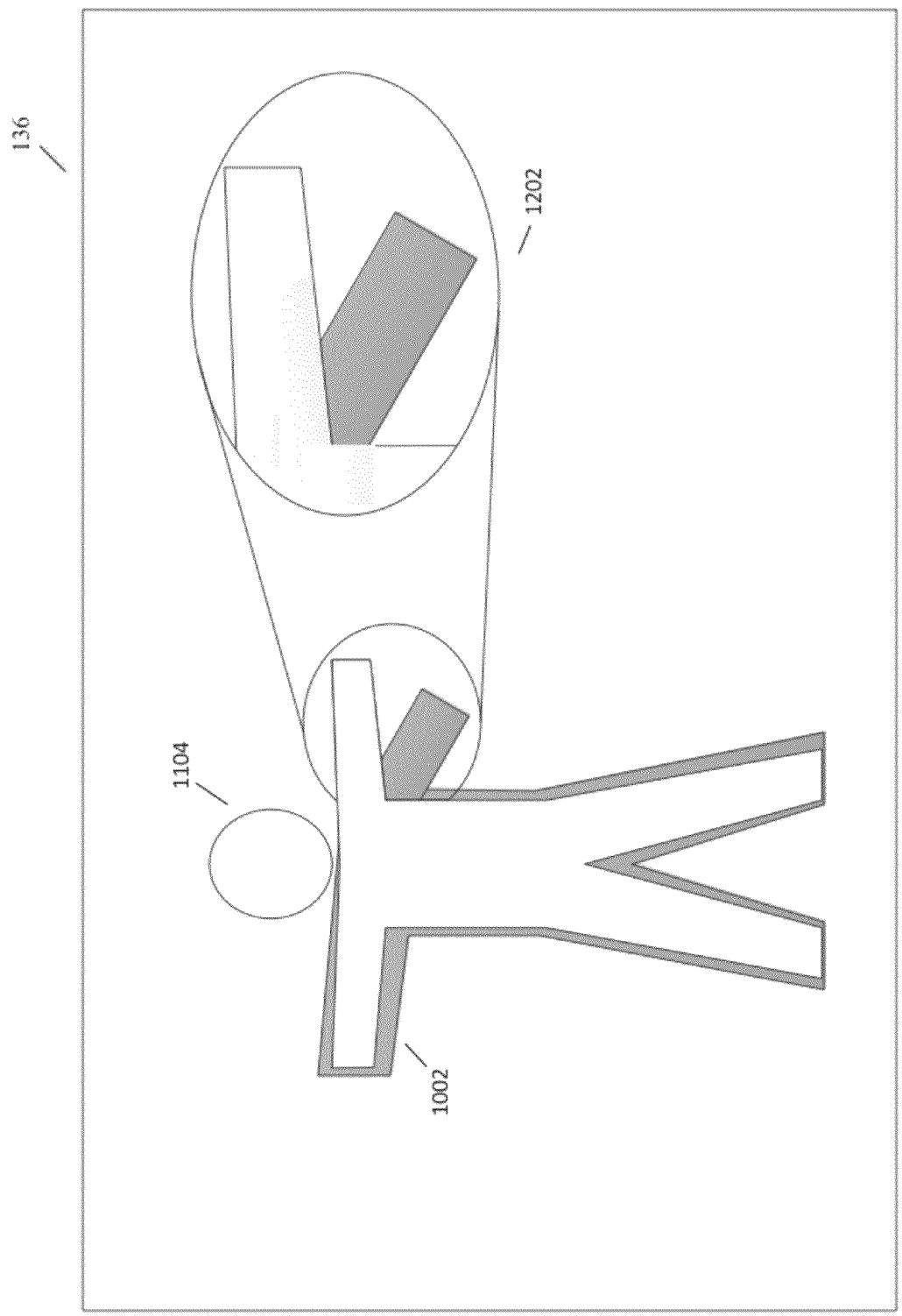
FIG. 12 illustrates an example display of a user avatar having a magnified inset in accordance with example embodiments.

FIG. 12 illustrates an example display of a user avatar having a magnified inset view providing feedback on improper form while performing athletic movements in accordance with example embodiments. For the one or more body parts identified as having improper form (e.g., such as an identified subsection 1102 shown in FIG. 11 having insufficient overlap with a virtual shadow 1006 and/or or falling within an unacceptable form zone), system 100 may provide one or more inset magnified views. For example, magnified view 1202 of FIG. 12 shows a body portion of the user avatar 802 that does not coincide (such as within a minimum threshold) with the virtual shadow 1104. As seen in FIG. 12, an arm of the user avatar 1104 is not located at the same position as a corresponding arm of the shadow 1002. This portion of the user avatar 1104 is presented in a magnified inset view 1202. The magnified inset view 1202 may also highlight the user avatar 1104 in a first color (e.g., red) to emphasize the problem.

In another aspect, computer 102 may provide a replay feedback mode permitting a user to review their performance of an exercise. In one example, computer 102 may determine instances in the video when overlap between the user avatar 902 and shadow 1102 decreased below a certain threshold. For example, computer 102 may process subsections 1202 of each image, or at least some of the images, of the video to identify a subsection where overlap between the user avatar 902 and shadow 1006 decreased below a threshold. System 100 may identify and store a predetermined number of preceding images from the video corresponding to the identified subsection 1102 and continue storing images from the video until the overlap between the user avatar 802 and shadow 1102 increases above the threshold. The stored images may be referred to as a variance sequence.

A color of the current form information, such as information 904 discussed above in relation to FIG. 9, may vary based on how well the user's form corresponds to desired form. For example, green may indicate less than a 5 degree angle between lines of the form guidance information 702 and the current form information 904, yellow may indicate a 5 degree to 15 degree angle between lines of the form guidance information 702 and the current form information 904, and red may indicate greater than a 15 degree angle between lines of the form guidance information 702 and the current form information 904.

II. Estimating Fatigue Values

Aspects of this disclosure further relate to estimating one or more fatigue values. In one embodiment, block 314 may be implemented to estimate a value based upon the user's performance during a movement and/or exercise monitored at block 306. In certain embodiments, a muscle fatigue value may be estimated. In other embodiments, a respiratory fatigue value may be estimated. In further embodiments, a plurality of fatigue values may be estimated. For example, a first fatigue value may be estimated for a first muscle group and a second fatigue value may be estimated for a second muscle group. Yet in another embodiment, a first muscle fatigue value and a first respiratory fatigue value may be estimated.

One or more values may be based, at least in part, on a degradation of form during the user's performance of a movement or exercise. In one embodiment, the number of variance sequences (or severity of sequences) collected during athletic movements, and one or more body parts involved causing the variance may be considered in estimating a fatigue value. In still yet in even further embodiments, a value may be based upon form degradation as well as data that may or may not be not utilized to determine (directly and/or indirectly) form degradation. Data that was not utilized to determine form degradation may be taken at a time period that is (at least partially) different than determinations relating to form degradation. For example, data obtained from sensors 138, 140, and/or 142 before, during, and/or after user 124 performs the monitored movement or exercise may be utilized in estimating a value. For example, if data taken from sensor 138 indicates that a user walked 10 miles and data taken from sensor 142 indicates that user 124 jumped a certain number of times, data may be utilized to determine a fatigue value, such as for the legs (or a portion thereof).

Figure 13:
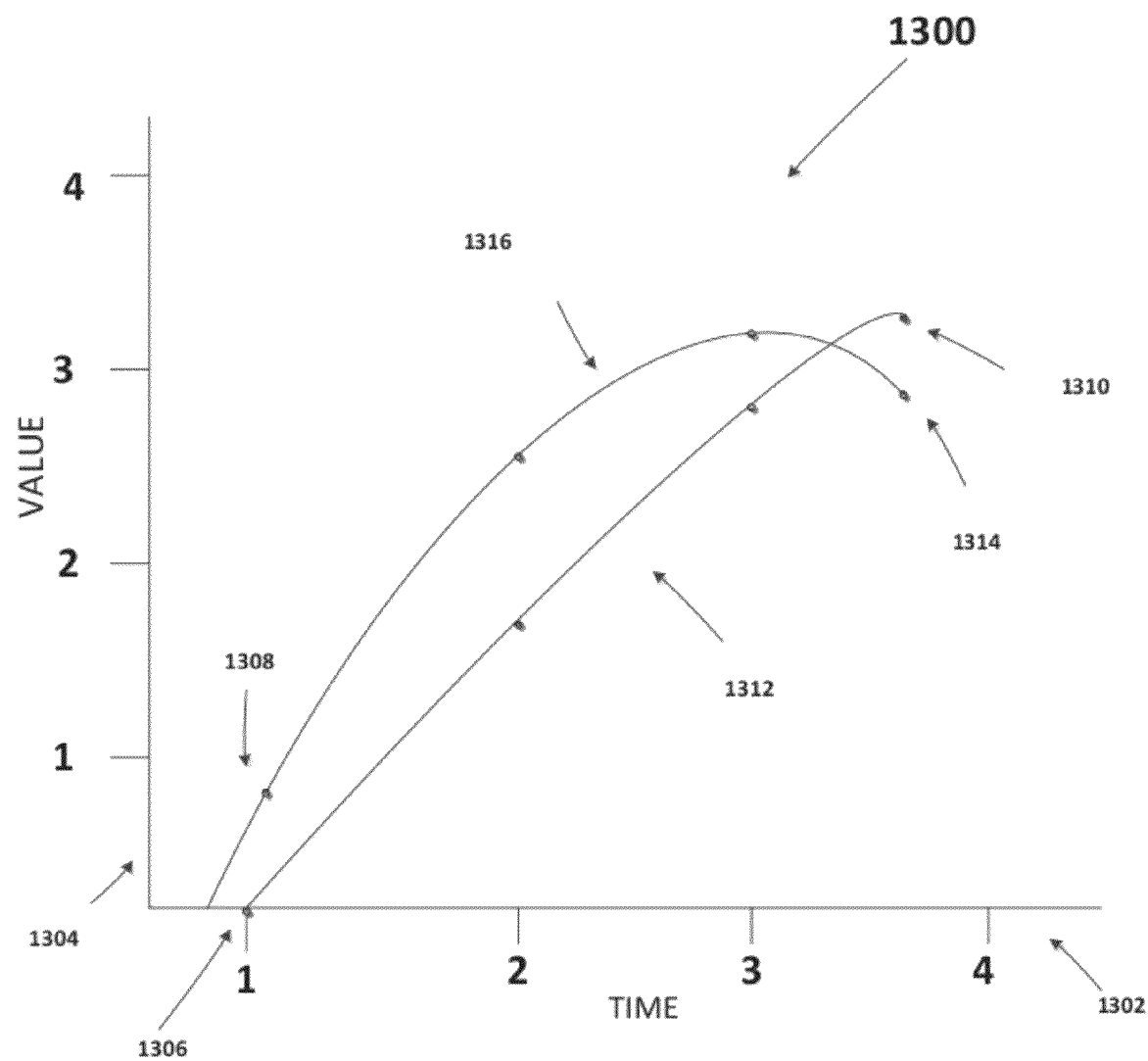
FIG. 13 shows an example chart of a two fatigue indices in accordance with an embodiment.

In this regard, multiple fatigue values may be estimated for the same time period. For example, block 314 may be implemented to estimate a fatigue value during performance of a first movement, such as that monitored during block 306. For example, as shown in chart 1300 of FIG. 13, a first movement and/or exercise may be associated with multiple fatigue values. Looking at FIG. 13, chart 1300's x-axis (1302) may relate to time. Time may be represented by fractions of a second, seconds, minutes, hours, or any other measurement of time. The y-axis (1304) may be any representative scale to measure fatigue. Those skilled in the art will appreciate that the axes may have more than one scale and/or measure more than one parameter. Similarly, the axes may be switched. As shown in chart, 1306 and 1308 may be taken at Time=1, however, may relate to different fatigue parameters, such as but not limited to: different muscle groups, respiratory fatigue, and combinations thereof.

Values for the same fatigue parameters may be utilized to form a fatigue index. (See block 316) For example, values 1306 and 1310 may be taken at different time periods during a single movement or exercise. For example, values 1306 and 1310 may mark the beginning and the end of an exercise or movement. In this regard, values 1306 and 1310 (alone or along with other values for the same fatigue parameter) may be utilized to form a first fatigue index, such as represented by line 1312 for that fatigue parameter.

Similarly, values 1308 and 1314 (alone or with other values) may be utilized in the formation of a second fatigue index, which may be represented by line 1316. As such, multiple different fatigue indexes can be formed during the same movement and/or exercise to measure different fatigue parameters, such as but not limited to: different muscle groups, respiratory fatigue, and combinations thereof (See block 316 and/or decision 318).

In certain embodiments, the fatigue index, such as index 1312 and/or 1316, may be utilized to provide further movements and/or exercises. In one embodiment, a fatigue index may be utilized in the formation or adjustment to a personalized workout plan. One or more fatigue indexes may be utilized in conjunction with an assessment, such as performed as part of block 302, to determine what movements and/or exercises to provide to user 124. At block 320, instructions to perform the next movement and/or exercise may be provided to the user. Example systems and methods for providing instructions were discussed in relation to block 304, which may be implemented, either in whole or in part, at block 320. Further fatigue values may be utilized as part of the fatigue index(es). (See, e.g., block 322).

Further aspects of this disclosure relate to the formulation of a cumulative or collective fatigue index that may consider fatigue across a plurality of distinct workouts or exercises. For example, in one embodiment, two workout sessions may be separated by, for example, by at least 30 minutes, 1 hour, 6 hours, 12 hours, 18 hours, 1 day, 3 days, 1 week, 10 days, 15 days, and/or a month. These are merely examples, and it should be understood that other time frames are within the realm of this disclosure. In one embodiment, a cumulative fatigue index may comprise at least one fatigue value obtained from a plurality of discrete workouts. Thus, in one implementation, block 324 may create or modify the cumulative fatigue index with at least one fatigue value from a fatigue index formulated at block 316. Thus, similar to the fatigue index of block 316, the cumulative fatigue index may comprise a value based upon a user's performance across a plurality of movements or exercises.

Determination of the cumulative index may consider the number of variance sequences collected during athletic movements for each workout session and/or one or more body parts involved causing the variance. In still yet in even further embodiments, a value may be based upon form degradation as well as data not utilized to determine (directly and/or indirectly) form degradation. Data that was not utilized to determine form degradation may be taken at a time period that is (at least partially) different than determinations relating to form degradation.

In certain embodiments, a fatigue index may be weighted according to one or more factors, including but not limited to: the type of exercise, difficulty level, time since the user last performed a movement, and combinations thereof. Thus, indexes (and/or values therein) may be weighted more heavily than others.

Based upon an index, including but not limited to the index constructed or modified as part of block 316 and/or the cumulative index created or modified as part of block 324, one or more instructions may be provided to the user. Exemplary instructions have been provided throughout this disclosure.

In further embodiments, it may be determined to modify a workout schedule (including, but not limited to frequency, exercises, difficulty/intensity of movements, or combinations thereof) to promote regeneration. A first modification may be designed to promote muscle regeneration and a second modification may be designed to promote a respiratory regeneration. As discussed above, multiple groups may be targeted, either simultaneously or individually. In one embodiment, the user may be instructed to perform one or more yoga exercises to promote respiratory and/or muscle regeneration. In another embodiment, one or more stretching exercises may be utilized. In further embodiments, one or more routines may be provided to encourage resting or reduced impact on certain groups, regions, or systems that may need regeneration while encouraging the user to utilize other groups, regions, or systems that may be less "depleted" or otherwise less in need of regeneration. As would be appreciated by those skilled in the art with the benefit of this disclosure, multiple activities may be selected/or be selectable to promote regeneration of one or more groups, regions and/or systems. In further embodiments, it may be determined to reassess user 124. Thus, an assessment, such as the assessment described as part of block 302 may be initiated.

In further embodiments, computer 102 (or any other electronic device) may also use a graphical representation, such as shadow 1102, to provide feedback to a user on proper form. To aid a user with their form, the graphical representation, such as virtual shadow 1102, may be used to present proper form to a user while the user 124 is performing the exercise, such as part of block 312. For instance, the virtual shadow 1102 may be created based on capturing data from a professional athlete or trainer demonstrating proper form for an exercise. While performing repetitions of an exercise, computer 102 may cause the display 136 to present the virtual shadow 1102 with proper exercise form relative to the user avatar 802. For instance, the virtual shadow 1102 may be depicted overtop of the user avatar 802, as shown in FIG. 12A, or offset from the user avatar 802, for example as shown in FIG. 12B. In an example, the virtual shadow 1102 may be an animation moved at the same pace as the user performing an exercise. In one embodiment, computer 102 is configured to alter the pace of an animation based on the user's performance of the exercise.

In certain embodiments, regeneration exercises may prompt user to interact with virtual targets. For example, display 136 may present multiple virtual targets which user 124 is instructed to place the hand, foot, or other part of their body. The virtual targets 1002 may be used to aid a user in having proper form. Thus, user 124 may be provided instructions that, if properly executed, encourage proper form and/or regenerate a muscle group and/or the respiratory system. For example, computer 102 may process video, sensor data, or infrared data for a user to determine if the user has placed the proper body part in the desired virtual target during performance of an exercise. Display 136 to highlight each of the targets in a certain color (e.g., green) and/or play an audible sound. In one embodiment, block 308 may comprise displaying a range of colors based upon the performance of the user. Ranges of coloration may be based upon performance thresholds. For example, a green coloration may be utilized in a user is above a 90% threshold, an orange coloration is utilized if the user is between an 89%-70% threshold, and a red coloration may be utilized if the user's performance falls below a 70% threshold. Similarly, different sounds may be utilized to provide feedback to the user. If not, system 100 may highlight each missed target and/or play an audible sound. Computer 102 may cause display 136 to display user avatar, such as avatar 902, highlighting the knees and/or any other problem area (e.g., different color, encircle one or more body parts, inset picture with enlarged view of problem area, etc.). Display 136 may display an instruction 1006 to correct the user's form (e.g., straighten knees).

CONCLUSION

Providing an activity environment having one or more of the features described herein may provide a user with an immersive experience that will encourage and motivate the user to engage in athletic activities and improve his or her fitness. Users may further communicate through social communities and challenge one another to reach various levels of fitness, and to view their fitness level and activity.

Aspects of the embodiments have been described in terms of illustrative embodiments thereof. In this regard, any of the portions of any flowchart disclosed may be rearranged, some blocks may be removed, additional blocks may be added, each block may be repeated one or more times, and the flow diagram may be repeated one or more times.

Numerous other embodiments, modifications and variations within the scope and spirit of the appended claims will occur to persons of ordinary skill in the art from a review of this disclosure. For example, one of ordinary skill in the art will appreciate that the steps illustrated in the illustrative figures may be performed in other than the recited order, and that one or more steps illustrated may be optional in accordance with aspects of the embodiments.

What is claimed is:

1. A computer-implemented method comprising:
providing first instructions to a user to perform an athletic movement comprising predefined criteria at a first location during a first time period;
detecting, with at least a first sensor, an item of apparel of the user performing the athletic movement corresponding to a position of a limb of the user at the first location;
constructing a form profile, wherein the form profile comprises a plurality of data points generated by the sensor during the athletic movement, wherein a selected data point, from the plurality of data points, comprises a location of a body part of the user in combination with a time stamp;
determining the user's performance of the predefined criteria, wherein the determining comprises comparing the form profile against a first profile template for the athletic movement; and
based upon the user's performance, estimating with a processor a muscle fatigue value.

2. The method of claim 1, further comprising:
based upon a determination that the muscle fatigue value exceeded a threshold, determining second instructions to provide the user to promote muscle regeneration.

3. The method of claim 1, wherein the muscle fatigue value comprises a first muscle group fatigue value for a first muscle group and a second muscle group fatigue value for a second muscle group.

4. The method of claim 3, further comprising:
based upon the first muscle fatigue value, determining second instructions to provide the user to promote muscle regeneration of the first muscle group.

5. The method of claim 4, further comprising:
determining third instructions to provide the user to promote muscle regeneration of the second muscle group.

6. The method of claim 3, wherein a plurality of muscle fatigue values are estimated during the first time period, the method further comprising:
constructing a fatigue index for the first period that associates at least a portion of the plurality of muscle fatigue values with a time stamp representative of a time of capture.

7. The method of claim 6, further comprising:
based upon the fatigue index, determining second instructions to provide the user to promote muscle regeneration of the first muscle group, and determining third instructions to provide the user to promote muscle regeneration of the second muscle group.

8. The method of claim 1, wherein the first sensor comprises an image capture device.

9. The method of claim 1, wherein the muscle fatigue value is a first muscle fatigue value, the method further comprising:
providing second instructions to a user to perform an athletic movement comprising predefined criteria at the first location during a second time period that is at least a predetermined value of time after the first time period;
monitoring with at least the first sensor the user performing the athletic movement at the first location, wherein the monitoring comprises determining a form profile of the user as a function of time for the athletic movement during the second time period;
determining the user's performance of the predefined criteria during the second time period, wherein the determining comprises comparing the form profile against a first profile template for the athletic movement; and based upon the user's performance during the first and the second time periods, estimating with a processor a second muscle fatigue value.

10. The method of claim 9, further comprising:
constructing a fatigue index comprising at least the first and the second fatigue values.

11. The method of claim 9, wherein a plurality of muscle fatigue values are estimated during both the first and the second time periods, the method further comprising:
constructing a fatigue index for the first period that associates at least a portion of the plurality of muscle fatigue values for the first time period with a time stamp representative of a time of capture;
constructing a second fatigue index for the second period that associates at least a portion of the plurality of muscle fatigue values for the second time period with a time stamp representative of a time of capture;
comparing the first fatigue index with the second fatigue index to estimate a cumulative fatigue index; and
based upon the cumulative fatigue index, determining second instructions to provide the user to promote muscle regeneration.

12. The method of claim 9, wherein the first time period and the second time period are separated by a value selected from the group consisting of: at least 30 minutes, at least 1 hour, at least 6 hours, at least 12 hours, at least 18 hours, at least 1 day, at least 3 days, at least 1 week, at least 10 days, at least 15 days, at least 1 month, and at least 1 year.

13. The method of claim 4, further comprising:
receiving from a second sensor, movement data collected during the user's performance of an athletic movement at a second location; and
utilizing at least a portion of movement data collected from the second location in estimating the fatigue value.

14. The method of claim 1, wherein the determining of the of the user's performance of the predefined criteria further comprises:
upon detecting a first variance from a form profile threshold, transmitting first instructions to the user providing motivation to complete the criteria; and
further detecting the user's performance of the predefined criteria.

15. The method of claim 14, further comprising:
detecting a second variance from a form profile threshold.

16. The method of claim 15, wherein the fatigue value is weighted upon at least one of the first and the second variances.

17. A computer-implemented method comprising:
providing first instructions to a user to perform an athletic movement comprising predefined criteria at a first location during a first time period;
detecting, with at least a first sensor, an item of apparel of the user performing the athletic movement corresponding to a position of a limb of the user at the first location;
constructing a first form profile, wherein the form profile comprises a plurality of data points generated by the sensor during the athletic movement, wherein a selected data point, from the plurality of data points, comprises a location of a body part of the user in combination with a time stamp;
determining that the user's performance does not meet at least one of the predefined criteria, wherein the determining comprises:
comparing the obtained first form profile against a form profile template for the athletic movement;
transmitting first instructions to the user providing motivation to complete the criteria;
further detecting the user's performance of the predefined criteria during a second time period comprising:
obtaining a second form profile of the user as a function of time during user's performance of the athletic movement; and
comparing the obtained second form profile against a form profile template for the athletic movement, and
estimating with a processor a muscle fatigue value based upon, at least in part, the user's performance at the first location during the first time period and the second time period.

18. The method of claim 17, wherein the muscle fatigue value is a first muscle fatigue value and the method further comprising:
continuing to monitor the user at the first location during the first time; and
generating a second muscle fatigue value.

19. The method of claim 18, further comprising:
based upon at least the first and the second muscle fatigue values, forming or modifying a fatigue index; and
determining, based upon the fatigue index, second instructions to provide the user to promote muscle regeneration.

20. A device configured to be worn on an appendage of a user comprising:
a processor;
a sensor; and
a non-transitory computer-readable medium comprising computer-executable instructions that when executed by the processor perform at least:
detecting with at least the sensor, an item of apparel of the user performing an athletic movement corresponding to a position of a limb of the user;
constructing a form profile, wherein the form profile comprises a plurality of data points generated during the athletic movement, and wherein a selected data point, from the plurality of data points, comprises a location of a body part of the user in combination with a time stamp;
determining the user's performance of the athletic movement, wherein the determining comprises comparing the form profile against a form profile template for the athletic movement; and
based upon the determination of the user's performance, calculating a muscle fatigue value with the processor of the device.

* * * * *